(12) United States Patent
Li et al.

(10) Patent No.: US 7,261,875 B2
(45) Date of Patent: Aug. 28, 2007

(54) DENDRITIC POLY (AMINO ACID) CARRIERS AND METHODS OF USE

(75) Inventors: Chun Li, Missouri City, TX (US); Wayne Tansey, Houston, TX (US); Chusilp Charnsangavej, Houston, TX (US); Sidney Wallace, Bellaire, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 528 days.

(21) Appl. No.: 10/327,455

(22) Filed: Dec. 20, 2002

(65) Prior Publication Data

US 2003/0232968 A1 Dec. 18, 2003

Related U.S. Application Data

(60) Provisional application No. 60/342,807, filed on Dec. 21, 2001.

(51) Int. Cl.
*A61K 51/00* (2006.01)
*A61M 36/14* (2006.01)

(52) U.S. Cl. .................... 424/1.69; 424/1.11; 424/1.65

(58) Field of Classification Search .............. 424/1.11, 424/1.65, 9.1, 484, 485, 486, DIG. 16, 1.69; 534/7, 10–16; 562/553, 516
See application file for complete search history.

(56) References Cited

U.S. PATENT DOCUMENTS

| | | | |
|---|---|---|---|
| 4,418,068 A | 11/1983 | Jones | 424/267 |
| 4,507,466 A | 3/1985 | Tomalia et al. | 528/332 |
| 4,558,120 A | 12/1985 | Tomalia et al. | 528/363 |
| 4,568,737 A | 2/1986 | Tomalia et al. | 528/332 |
| 4,587,329 A | 5/1986 | Tomalia et al. | 528/363 |
| 4,631,337 A | 12/1986 | Tomalia et al. | 528/391 |
| 4,694,064 A | 9/1987 | Tomalia et al. | 528/332 |
| 4,713,975 A | 12/1987 | Tomalia et al. | 73/865.8 |
| 4,732,863 A | 3/1988 | Tomasi et al. | 436/547 |
| 4,737,550 A | 4/1988 | Tomalia | 525/418 |
| 4,857,599 A | 8/1989 | Tomalia et al. | 525/259 |
| 4,871,779 A | 10/1989 | Killat et al. | 521/28 |
| 4,988,496 A | 1/1991 | Srinivasan et al. | 424/1.1 |
| 5,087,616 A | 2/1992 | Myers et al. | 514/21 |
| 5,108,921 A | 4/1992 | Low et al. | 435/240.1 |
| 5,164,294 A | 11/1992 | Skold et al. | 435/7.5 |
| 5,279,811 A | 1/1994 | Bergstein et al. | 424/1.1 |
| 5,412,072 A | 5/1995 | Sakurai et al. | 530/322 |
| 5,416,016 A | 5/1995 | Low et al. | 435/240.1 |
| 5,517,993 A | 5/1996 | Unger et al. | 128/653.4 |
| 5,534,241 A | 7/1996 | Torchilin et al. | 424/9.321 |
| 5,602,112 A | 2/1997 | Rubinfeld | 514/58 |
| 5,605,671 A | 2/1997 | Lyle et al. | 424/1.41 |
| 5,635,382 A | 6/1997 | Low et al. | 435/172.3 |
| 5,635,603 A | 6/1997 | Hansen et al. | 530/391.5 |
| 5,670,132 A | 9/1997 | Griffiths et al. | 424/1.11 |
| 5,688,488 A | 11/1997 | Low et al. | 424/1.69 |
| 5,730,968 A | 3/1998 | Butterfield et al. | 424/78.37 |
| 5,820,847 A | 10/1998 | Low et al. | 424/9.1 |
| 5,830,431 A | 11/1998 | Srinivasan et al. | 424/1.69 |
| 5,908,777 A | 6/1999 | Lee et al. | 435/320.1 |
| 5,951,964 A | 9/1999 | Dean et al. | 424/1.69 |
| 5,955,053 A | 9/1999 | Marzilli et al. | 424/1.11 |
| 5,977,163 A | 11/1999 | Li et al. | 514/449 |
| 5,986,074 A | 11/1999 | Marzilli et al. | 534/14 |
| 6,071,533 A | 6/2000 | Papahadjopoulos et al. | 424/450 |
| 6,083,741 A | 7/2000 | Hart et al. | 435/320.1 |
| 6,103,487 A | 8/2000 | Barnett et al. | 435/15 |
| 6,113,946 A | 9/2000 | Szoka, Jr. et al. | 424/486 |
| 6,197,278 B1 | 3/2001 | Blankenberg et al. | 424/1.69 |
| 6,251,866 B1 | 6/2001 | Prakash et al. | 514/17 |
| 6,262,107 B1 | 7/2001 | Li et al. | 514/449 |
| 6,733,755 B2 | 5/2004 | Tchistiakova et al. | 424/185.1 |
| 2001/0034363 A1 | 10/2001 | Li et al. | 514/449 |
| 2001/0041189 A1 | 11/2001 | Xu | 424/488 |

FOREIGN PATENT DOCUMENTS

| | | |
|---|---|---|
| EP | 0554708 | 1/1993 |
| EP | 0693073 | 3/1994 |
| WO | WO95/28966 | 11/1995 |
| WO | WO97/33552 | 9/1997 |
| WO | WO99/39748 | 8/1999 |

(Continued)

OTHER PUBLICATIONS

Higashi et al (Chem. Commun., 2000, 361-362).*
International PCT Search Report PCT/US02/40937, 9 pages, Mailed Apr. 4, 2003.
Aoi, K., et al. "Globular Carbohydrate Macromolecule 'Sugar Balls' 3. 'Radical-Growth Polymerization' of Sugar-Substituted α-Amino Acid N-Carboxyanhydrides (GlycoNCAs) with a Dendritic Initiator"; Tetrahedron, Elsevier Science Publishers, Amsterdam, NL, vol. 53, No. 45; pp. 15415-15427, Nov. 10, 1997.

(Continued)

*Primary Examiner*—Dameron L. Jones
(74) *Attorney, Agent, or Firm*—Baker Botts L.L.P.

(57) ABSTRACT

The present invention concerns a design for dendritic poly (amino acid) polymer carriers, also known as nonlinear polymers, and their applications. These dendritic poly (amino acid) carriers have multiple functional groups at the polymer surface. In addition, they have heterofunctional groups on the poly(amino acid) side chains for drug or diagnostic agent attachment. They are designed to allow sufficient preservation of the binding affinity of the targeting ligand while conjugating therapeutic or diagnostic agents to the polymers. The present invention also describes methods of production of the polymer carriers and methods for the treatment or diagnosis of diseases employing the polymer carriers. The present invention also includes methods to introduce targeting moieties site-specifically to the end of polymer chains.

42 Claims, 10 Drawing Sheets
(2 of 10 Drawing Sheet(s) Filed in Color)

FOREIGN PATENT DOCUMENTS

| WO | WO99/49901 | 10/1999 |
| --- | --- | --- |
| WO | WO99/61512 | 12/1999 |
| WO | 00/02587 | 1/2000 |
| WO | WO 00/53233 | 9/2000 |
| WO | WO 00/61788 | 10/2000 |
| WO | WO 01/91807 | 12/2001 |
| WO | 02/077036 | 10/2002 |

OTHER PUBLICATIONS

Hudecz, F., et al. "Influence of Carrier on Blodistribution and in Vitro Cytotoxicty of Methotrexate-Branched Polypeptide Conjugates", Bioconjugate Chemistry, American Chemical Society; vol. 4, No. 1, pp. 25-33, Jan. 1993.

Pimm, M.V. et al. "Strategies for Labelling Branched Polypeptides with a Poly (L-Lysine) Backbone with Radioiodines $^{123}$I, $^{125}$I, $^{131}$I) and Radiometals ($^{111}$In, $^{51}$Cr) for Biodistribution Studies and Redlopharmaceutical Development", Journal of Labelled Compounds and Radiopharmaceuticals; vol. 36 No. 2, pp. 157-172, 1995.

Brokx, R., et al. "Designing peptide-based scaffolds as drug delivery vehicles", Science Publishers B.V. Amsterdam, vol. 78 No. 1-3, pp. 115-123, Jan. 17, 2002.

Klok, H. et al. "Star-Shaped Fluorescent Polypeptides", Journal of Polymer Science, vol. 39 No. 10, pp. 1572-1582, Feb. 20, 2001.

Gariepy, J. et al. "A Novel Method of Conjugation of Daunomycin with Antibody with a Poly-L-glutamic Acid Derivative as Intermediate Drug Carrier, An Anti-α-fetoprotein Antibody-Daunomycin Conjugate", Journal of Medicinal Chemistry, vol. 27 No. 12, pp. 1602-1607, 1984.

Gariepy J. et al. "Vectorial delivery of macromolecules into cells using peptide-based vehicles", Trends in Biotechnology, vol. 19 No. 1, pp. 21-28, Jan. 1, 2001.

PCT International Preliminary Examination Report for International Application No. PCT/US02/12502, 6 pages, Mailing Date Oct. 13, 2004.

PCT International Preliminary Examination Report for International Application No. PCT/US02/40937, 4 pages, Mailing Date Oct. 19, 2004.

PCT International Search Report PCT/US02/12502. 7 pages, Mailed Oct. 9, 2003.

Benns et al., "Tailoring new gene delivery designs for specific targets". Journal of Drug Targeting, vol. 8, No. 1 Database Medline on STN International, Accession No. 2000222278. 2 pages, 2000.

Blair et al., "Linkage of Cytotoxic Agents to Immunoglobulins". Journal of Immunological Methods, vol. 59, pp. 129-143, 1983.

Greenfield et al., "In Vitro Evaluation of Immunoconjugates Prepared by Linking Mitomycin C to Monoclonal Antibodies via Polyglutamic Acid Carriers". Antibody, Immunoconjugates, and Radiopharmaceuticals. vol. 2, No. 3, pp. 201-216, 1989.

International PCT Search Report PCT/US02/12510, 6 pages, Mailed Sep. 12, 2003.

Anderson et al. "*Radiometal-Labeled Agents (Non-Technetium ) for Diagnostic Imaging*" Chem. Rev. vol. 99 pp. 2219-2234, 1999.

Bajorin et al. Proceedings of the American Society of Clinical Oncology American Society of Clinical Oncology, Inc., vol. 7, p. 250, Mar. 1988.

Baselga et al. "*Phase I Studies of Anti-Epidermal Growth Factor Receptor Chimeric Antibody C225 Alone and in Combination with Cisplatin*" J Clinical Oncology vol. 18 pp. 904-914, 2000.

Baselga et al. "*Recombinant Humanized Anti-HER2 Antibody (Herceptin) Enhances the Antitumor Activity of Paclitaxel and Doxorubicin Against HER2/New Overexpressing Human Breast Cancer Xenografts*" Cancer Research vol. 58 pp. 2825-2831, 1998.

Blackenberg et al. "*Apoptosis: The Importance of Nuclear Medicine*" Nucl. Med. Comm. vol. 21 pp. 241-250, 2000.

Blackenberg et al. "In Vivo *Detection and Imaging of Phosphatidylserine Expression During Programmed Cell Death*" Proc. Natl. Acad. Sci. USA vol. 95 pp. 6349-6354, 1998.

Blackenberg et al. "*Imaging of Apoptosis (Programmed Cell Death) with TC Annexin V*" J. Nuclear Medicine vol. 40 pp. 184-191, 1999.

Block et al. "*Poly(g-benzyl-L-glutamate) and Other Glutamic Acid Containing Polymers*" Gordon and Breach Science Publishers, NY p. 11-31, 1983.

Bohdiewicz et al. "*Indium-111 Satumomab Pendetide: The First FDA-Approved Monoclonal Antibody for Tumor Imaging*" J Nuclear Medicine Technology vol. 26 pp. 155-163, 1998.

Brechbiel et al. "*Synthesis of 1 (P-Isothiocyanatobenzyl) Derivatives of DTPA and EDTA. Antibody Labeling and Tumor-Imaging Studies*" Inorg Chem. vol. 25 pp. 2772-2781, 1986.

Chapman et al. "*Therapeutic Antibody Fragments Iwth Prolonged in vivo Half-Lives*" Nature Biotech. vol. 17 pp. 780-783, 1999.

Collier et al. "*Immunoscintlgraphy Performed with In-111-Labeled CYT-103 in the Management of Coloretal Cancer: Comparison with CT*" Radiology vol. 185 pp. 179-186, 1992.

Culver et al. "In vivo *Gene Transfer with Retroviral Vector-Producer Cells for Treatment of Experimental Brain Tumors*" Science vol. 256 pp. 1550-1552, 1992.

Deguchi et al. *Retention of Biologic Activity of Human Epidermal Growth Factor Following Conjugation to a Blood-Brain Barrier Drug Delivery Vector Via an Extended Poly(ethylene glycol)*, 1999.

DeNardo et al. "*Pharmacokinetics of Chimeric L6 Conjugated to Indium 111-and Yttrium-90-DOTA-Peptide In Tumor-Bearing Mice*" J Nuclear Medicine vol. 36 pp. 829-836, 1995.

DeNardo et al. "*Yttrium-90/Indoum-111-DOTA-Peptide-Chimeric L6: Pharmacokinetics, Dosimetry and Intitial Results in Patients with Incurable Breast Cancer*" Anticancer Research vol. 17 pp. 1735-1744, 1997.

Deutsch et al. "*Synthesis of congeners and Prodrugs, Water-Soluble Prodrugs of Taxol with Potent Antitumor Activity*" J. Med. Chem. vol. 32, pp. 788-792, 1989.

Divgi et al. "*Phase I and Imaging Trial of Indium 111-Labeled Anti-Epidermal Growth Factor Receptor Monoclonal Antibody 225 In Patients with Squamous Cell Lung Carcinoma*" J. National Cancer Institute vol. 83 pp. 97-104, 1991.

Drobnik et al. "*Soluble Synthetic Polymers In Biological Systems*" Adv. Polym. Sci, vol. 57 pp. 1-50, 1984.

Dunn et al. "*Receptor-Mediated Endocytosis of Epidermal Growth Factor By Hepatocytes in the Perfused Rat Liver; Ligand and Receptor Dynamics*" J Cell Biol. vol. 98 pp. 2148-2159, 1984.

Eary et al. "*Radiochemistry of Halogenated Antibodies*" Antibodies in Radiodiagnosis and Therapy, Boca Ratan, Florida, CPC Press pp. 83-100.

Eiseman et al. "*Plasma Pharmacokinetics and Tissue Distribution of Paclitaxel in CD2F1 Mice*" Cancer Chemother. Pharmacol. vol. 34 pp. 465-471, 1994.

Ennis et al. "*Anti-Epidermal Growth Factor Receptor Antibodies Inhibit the Autocrine-Stimulated Growth of MDA-468 Human Breast Cancer Cells*" Mol. Endocrinology vol. 3 pp. 1830-1838, 1989.

Ethier "*Growth Factor Synthesis and Human Breast Cancer Progression*" J Natl Cancer Inst. vol. 87 pp. 964-973, 1995.

Fan et al. "*Antitumor Effect of Anti-Epidermal Growth Factor Receptor Monoclonal Antibodies Plus Cis-Diamminedichloroplatinum on Well Established A431 Cell Xenografts*" Cancer Research vol. 53 pp. 4637-4642, 1993.

Fan et al. "*Blockage of Epidermal Growth Factor Receptor Function by Bivalent and Monovalent Fragments of 225 Anti-Epidermal Growth Factor Receptor Monoclonal Antibodies*" Cancer Research vol. 53 pp. 4322-4328, 1993.

Fang et al. "*Involvement of p21 Waff in mediating Inhibition of Paciltaxel-Induced Apoptosis by Epidermal Growth Factor in MDA-MB-468 Human Breast Cancer Cells*" Anticancer Research vol. 20 pp. 103-112, 2000.

Fidler et al. "*The biology of Cancer Invasion and Metastasis*" Adv. Cancer Res. vol. 28 pp. 149-250, 1987.

Foa et al. "*Taxol (paclitaxel): A Novel Anti-Microtubule Agent with Remarkable Anti-Neoplastic Activity*" J. Clin. Lab. Res. vol. 24 pp. 6-14, 1994.

Fuertges et al. "*The Clinical Efficacy of Poly(ethylene Glycol)-Modified Proteins*" J Controlled Release vol. 11 pp. 139-148, 1990.

Fuller et al. "*A Procedure for the Faclie Synthesis of Amino-Acid N-Carboxyanhydride*" Biopolymers vol. 15 p. 1869-1871, 1976.

Gabizon "*Selective Tumor Localization and Improved Theapeutic Index of Anthracyclines Encapsulated in Long-Circulating Liposomes*" Cancer Research vol. 52 pp. 891-896, 1992.

Goldenberg "*Monoclonal Antibodies In Cancer Detection and Therapy*" Am J Med vol. 94 pp. 297-312, 1993.

Goldenberg et al. "*Imaging of Human Tumor Xenografts with an Indium-111-Labeled Anti-Epidermal Growth Factor Receptor Monoclonal Antibody*" J National Cancer Institute vol. 81 pp. 1616-1625, 1989.

Goldspeil "*Pharmaceutical Issues: Preparation, Administration, Stability, and Compatibility with Other Medications*" Ann. Pharmacother. vol. 28 pp. S23-S26, 1994.

Gonda "*Aerosols for Delivery of Therapeutic and Diagnostic Agents to the Reparatory Tract*" Critical Reviews in Therapeutic Drug Carrier Systems vol. 6 pp. 273-313, 1990.

Greenwald et al. "*Drug Delivery Systems: Water Soluble Taxol 2'-poly(ethylene glycol) ester Prodrugs-Design and In Vivo Effectiveness*" J. Med. Chem. vol. 39 pp. 424-431, 1996.

Halpern et al. "*Stability, Characterization, and Kinetics of In-Labeled Monoclonal Antitumor Antibodies in Normal Animals and Nude Mouse Human Tumor Models*" Cancer Research vol. 43 pp. 5347-5355, 1983.

Hermanson "*Amine Detection Reagents*" Bioconjugate Techniquest, San Diego, Academic Press, pp. 112-114, 1996.

Hermanson "*Eliman's Assay for the Determination of Sulfhydryls*" Bioconjugate Techniques, San Diego, Academic Press, pp. 88-90, 1996.

Hnatowich et al. "*Radioactive Labeling of Antibody: A Simple and Efficient Method*" Science vol. 220 pp. 613-615, 1983.

Hoes et al. "*Optimization of Macromoledular Prodrugs of the Antitumor Antibiotic Adriamycin*" J. Controlled Release vol. 2 pp. 205-213, 1985.

Holmes et al. "*Current Status of Clinical Trials with Paclitaxel and Docetaxel, Taxane Anticancer Agents: Basic Science and Current Status*" American Chemical Society, Washington, DC pp. 31-57, 1995.

Inoue et al. "*Paciltaxel Enhances the Effects of the Anti-Epidermal Growth Factor Receptor Monocloncal Antibody ImClone C225 In Mice with Metastatic Human Bladder Transitional Cell Carcinoma*" Clinical Cancer Res. vol. 6 pp. 4874-4884, 2000.

Irie et al. "*Regression of Cutaneous Metastatic Melanoma by Intralesional Injection with Human Monoclonal Antibody to Ganglioside GD2*" Proc. Nat. Acad. Science USA vol. 83 pp. 8694-8698, 1986.

Jeppesen et al. "*Impact of Polymer Tether Length on Multiple Ligand-Receptor Bond Formation*" Science vol. 293 pp. 465-468, 2001.

Jurisson et al. "*Potential Technitium Small Molecule Radiopharmaceuticals*" Chem. Rev. vol. 99 pp. 2205-2218, 1999.

Kato et al. "*A Novel Method of Conjugation of Daunomycin with Antibody witha Poly-L-Glutamic Acid Derivative as Intermediate Drug Carrier. An Anti-α-fetoproten Antibody-Daunomycin Conjugate*" J. Med. Chem. vol. 27 pp. 1602-1607, 1984.

Kitamura et al. "*Chemical Engineering of the Monoclonal Antibody A7 by Polyethylene Glycol for Targeting Cancer Chemotherapy*" Cancer Research vol. 51 pp. 4310-4315, Accepted Jun. 5, 1991.

Kopecek et al. "*Targetable Water-Soluble Polymeric Anticancer Drugs: Achievements and Unsolved Problems*" Proceed Intern. Symp. Contol. Rel. Bioact. Mater vol. 20 pp. 190-191, 1993.

Kopecek "*The Potential of Water-Soluble Polymeric Carriers in Targeted and Site-Specific Drug Delivery*" Journal of Controlled Release vol. 11 pp. 279-290, 1990.

Kopecek et al. "*Targetable Polymeric Prodrugs*" J. Control. Release vol. 6 pp. 315-327, 1987.

Lamki "*Radioimmunoscintigraphy of Cancer,. Problems, Pitfalls, and Prospects*" Nuclear Medicine Annual 1990, New York, Raven Press Ltd. pp. 113-150, 1990.

Larson et al. "*Overview of Clinical Radioimmunodetection of Human Tumors*" Cancer vol. 73 (Suppl) pp. 832-835, 1994.

Li et al. "*Antitumor Activity of Poly (L-glutamic acid)-paclitaxel on Syngeneic and Xenografter Tumors*" Clinical Cancer Res. vol. 5 pp. 891-897, 1999.

Li et al. "*Complete Regression of Well-Established Tumors Using a Novel Water-Soluble Poly (L-glutamic acid)-paclitaxel Conjugate*" Cancer Res. vol. 58 pp. 2404-2409, 1998.

Li et al. "*Poly(L-glutamic acid)-Anticancer Drug Conjugates*" Advanced Drug Delivery Rev., vol. 54 pp. 695-713, 2002.

Li et al. "*Synthesis and Evaluation of Water-Soluble Polyethylene Glycol Pacilitaxel Conjugate as a Paclitaxel Prodrug*" Anti-Cancer Drugs, in press 1996.

Li et al. "*Synthesis, Metal Chelate Stability Studies, and Enzyme Digestion of a Peptide-Linked DOTA Derivative and its Corresponding Radiolabeled Immunoconjugates*" Bioconjugate Chem vol. 4, pp. 275-283, 1993.

Liu et al. "*$^{99m}$Tc-Labeled Small Peptides as Diagnostic Radiopharmaceuticals*" Chem Rev. vol. 99 pp. 2235-2268, 1999.

Liu et al. "*Bifunctional Chelators for Therapeutic Lanthanide Radiopharmaceuticals*" Bioconjugate Chemistry vol. 12 pp. 7-34, 2001.

Liu et al. "*Induction of Apoptosis and Activation of the Caspase Cascade by Anti-EGF Receptor Monoclonal Antibodies in DIFI Human Colon Cancer Cells Do Not Involve the C-jun N-Terminal Kinase Activity*" British Journal of Cancer vol. 82 pp. 1991-1999, 2000.

Lu et al. "*Polymerizable Fab Antibody Fragments for Targeting of Anticancer Drugs*" Nat. Biotech. vol. 17 pp. 1101-1104, 1999.

Maeda "*SMANCS and Polymer-Conjugated Macromolecular Drugs: Advantages in Cancer Chemotherapy*" Adv. Drug Delivery Rev. vol. 6 No. 2 pp. 181-202, 1991.

Maeda et al. "*Tumoritropic and Lymphotropic Principles of Macromolecular Drugs*" Crit. Rev. Ther. Drug Carrier Syst. vol. 6 pp. 193-210, 1989.

Mann et al. "*Molecular Amplifiers:Synthesis and Functionalization of a Ply(aminopropyl)dextran Bearing a Uniquely Reactive Terminus for Univalent Attachment of Biomolecules*" Bioconjugate Chem. vol. 3 pp. 154-159, 1992.

Masui et al "*Growth Inhibition of Human Tumor Cells in Athymic Mice by Anti-Epidermal Growth Factor Receptor Monoclonal Antibodies*" Cancer Research vol. 44, pp. 1002-1007, 1984.

Mathew et al. "*Synthesis and Evaluation of Some Water-Soluble Prodrugs and Derivatives of Taxol with Antitumor Activity*" J. Med. Chem. vol. 35 pp. 145-151, 1992.

Meares et al. "*Macrocyclic Chelates of Radiometals for Diagnosis and Therapy*" British J. Cancer. vol. 62 pp. 21-26, 1990.

Mendelsohn "*Epidermal Growth Factor Receptor Inhibition by a Monoclonal Antibody as Anticancer Therapy*" Clinical Cancer Research vol. 3 pp. 2703-2707, 1997.

Mendelsohn et al. "*Anti-Epidermal Growth Factor Recepotr Monoclonal Antibodies May Inhibit A431 Tumor Cell Proliferation by Blocking Autocrine Pathway*" Trans Assoc. Am Phys. vol. 100 pp. 173-178, 1987.

Miltross et al. "*Relationship of Mitotic Arrest and Apoptosis to Antitumor Effect of Paclitaxel*" J. National Cancer Institute vol. 88(18) pp. 1308-1314, 1996.

Mitchell et al. "*Active-Specific Immunotherapy for Melanoma*" J Clin. Oncol. vol. 8(5) pp. 856-869, 1990.

Modjahedi et al. "*The receptor for EGF and its Ligands: Expression, Prognostic Value and Target for Therapy in Cancer (Review)*" Int J Oncology vol. 4 pp. 277-296, 1994.

Morton et al. "*Prolongation of Survival in Metastatic Melanoma After Active Specific Immunotherapy with a New Polyvalent Melanoma Vaccine*" Annals of Surgery vol. 216(4) pp. 463-482, 1992.

Mosmann "*Rapid Colorimetic Assay for Cellular Growth and Survival: Application to Proliferation and Cytotoxicity Assay*" J. Immunol. Methods vol. 65 pp. 55-63, 1983.

Nicolaou et al. "*Design, Synthesis and Biological Activity of Protaxols*" Nature vol. 364 pp. 464-466, 1993.

Oldham et al. "*Comparison of Action of Paclitaxel and Poly (L-Glutamic acid)-Paclitaxel Conjugate in Human Breast Cancer Cells*" Int. J. Oncol. vol. 16 pp. 125-132, 2000.

Omelyaneko et al. "*HPMA Copolymer-Anticancer Drug-OV-TL16 Antibody Conjugates. Incluence of the Method of Synthesis on the Binding Affinity to OVCAR-3 Ovarian Carcinoma Cells In Vitro*" J. Drug Targeting vol. 3 pp. 357-373, 1996.

Omelyaneko et al. "*HPMA Copolymer-Anticancer Drug-OV-TL16 Antibody Conjugates. II. Processing in Epithelial Ovarian Carcinoma Cells In Vitro*" Int. J. Cancer vol. 75 pp. 600-608, 1998.

Ozanne et al. "*Over-Expression of the EGF Receptor is a Hallmark of Squamous Cell Carcinomas*" J. Pathol. vol. 149 pp. 9-14, 1986.

Pedley et al. "*The Potential for Enhanced Tumour Localisation by Poly(Ethylene Glycol) Modification of Anti-CEA Antibody*" British J. Cancer vol. 70 pp. 1126-1130, Revised Aug. 12, 1994.

Petrak et al. "*Transport of Macromolecules Across the Capillary Walls*" Adv. Drug Deliv. Rev. vol. 3 pp. 191-214, 1989.

Phillips-Hughes et al. "*Restenosis: Pathophysiology and Preventive Strategies*" JVIR vol. 7 pp. 321-333, 1996.

Pietersz et al. "*Specific In Vitro Anti-Tumor Activity of Methotrexate-Monoclonal Antibody Conjugates Prepared Using Human Serum Albumin as an Intermediary*" Immunol. Cell. Biol. vol. 66 pp. 43-49, 1988.

Pimm et al. "*Differences in Tumor and Normal Tissue Concentrations of Iodine and Indium Labeled Monoclonal Antibody II, biodistribution Studies in Mice with Human Tumor Xenografts*" Dur. J. Nucl. Med. vol. 11 pp. 300-304, 1985.

Potamianos et al. "*Radioimmunoscintigraphy and Radioimmunotherapy in Cancer: Principles and Application*" Anticancer Research vol. 20 pp. 925-948, 2000.

Putnan et al. "*Polymer Conjugates with Anticancer Activity*" Adv. Polym Science vol. 122 pp. 55-123, 1995.

Quadri et al. "*Effects of Linker Chemistry on the Pharmacokinetics of Radioimmunoconjugates*" Quart. J. Nucl. Med. vol. 42 pp. 250-261, 1998.

Ravindranath et al. "*Quantitation of the Density of Cell Surface Carbohydrate Antigens on Cance Cells with a Sensitive Cell-Suspension ELISA*" J Immunological Methods vol. 197 pp. 51-67, 1996.

Reilly et al. "*A Comparison of EGF and Mab 528 Labeled with in for Imaging Human Breast Cancer*" J Nucl. Med. vol. 41 pp. 903-911, 2000.

Rihova et al. "*Antiproliferative Effect of a Lectin- and Anti-Thy-1.2 Antibody-Targeted HPMA Copolymer-Bound Doxorubicin on Primary and Metastatic Human Colorectal Carcinoma and on Human Colorectal Carcinoma Trasfected with the Mouse Thy-1.2 Gene*" Bioconjugate Chemistry vol. 11 pp. 664-673, 2000.

Rosenberg et al. "*Experience with the Use of High-Dose Interleukin-2 in the Treatment of 652 Cancer Patients*" Annals of Surgery, vol. 210 No. 4 pp. 474-485, 1989.

Roth et al. "*Gene Therapy for Cancer: What Have the Inventors Done and where are the Inventors Going?*" J Natl. Can. Inst. vol. 89(1) pp. 21-39, 1997.

Rowinsky et al. "*Paclitaxel (Taxol)*" New England. J. Medicine vol. 332 pp. 1004-1014, 1995.

Rowinsky et al. "*Phase I and Pharmacologic Study of Paclitaxel and Cisplatin with Granulocyte Colony-Stimulating Factor: neuromuscular Toxicity is Dose-Limiting*" J. Clin. Oncol. vol. 11(10) pp. 2010-2020, 1993.

Rowland et al. "*Suppression of Tumor Growth in Mice by Drug-Antbody Conjugate Using a Novel Approach to Linkage*" Nature vol. 255 pp. 487-488, 1975.

Sabbatini et al. "*Early Findings in a Phase I Study of PG-Paclitaxel (CT-2103) In Recurrent Ovarian or Primary Peritoneal Cancer*" Proc. AACR-NCI-EORTC Int. Conference on Molecule Targets and Cancer Therapeutics, Abs vol. 470 p. 96, 2001.

Serruys et al. "*A Comparison of Balloon-Expandable-Stent Implantation with Baloon Angioplasty in Patients with Coronary Artery Disease*" New England J. Medicine vol. 331(8) pp. 489-495, 1994.

Seymour et al. "*Synthetic Polymers Conjugated to Monoclonal Antibodies: Vehicles for Tumor-Targeted Drug Delivery*" Selective Cancer Therapeutics vol. 7(2) pp. 59-73, 1991.

Shih et al. "*Anthracycline Immunoconjugates Prepared by a Site-Specific Linkage Via an Amino-Dextran Intermediate Carrier*" Cancer Research vol. 51 pp. 4192-4198, 1991.

Shimada et al. "*Biodistribution of Liposomes Containing Synthetic Galactose-Terminated Dlacylglyceryl-Poly(Ethyleneglycol)s*" Biochimica et Biophysica Acta vol. 1326 pp. 329-341, 1997.

Smith and Rutledge, Remington's Pharmaceutical Sciences, 18th Edition, Mack Printing Company, 1990.

Surwit et al. "*Clinical Assessment of In-CYT-103 Immunoscrintigraphy in Ovarian Cancer*" Gynecol Oncol vol. 48 pp. 285-292, 1993.

Takashina et al. "*Comparative Pharmacokinetic Properties of Murine Monoclonal Antibody A7 Modified with Neocarzinostatin, Dextran and Polyethylene Glycol*" Jpn J Cancer Res vol. 82 pp. 1145-1150, 1991.

Tam "*Synthetic Peptide Vaccine Design: Synthesis and Properties of a High-Density Multiple Antigenic Peptide System*" Proc. Natl. Academy of Science USA, vol. 85 pp. 5409-5413, 1988.

Tomalia et al. "*Starburst Dendrimers: Molecular-Level Control of Size, Shape, Surface Chemistry, Topology, and Flexibility from Atoms to Macroscopic Matter*" Angew. Chem. Int. Ed. Engl. vol. 29 pp. 138-175, 1990.

Torchilin et al. "*Chelating Polymer Modified Monoclonal Antibodies for Radioimmunodiagnostics and Radioimmunotherapy*" J Controlled Release vol. 24 pp. 111-118, 1993.

Van Heeswijk et al. "*The Synthesis and Characterization of Polypeptide-Adriamycin Conjugates and its Complexes with Adriamycin. Part I*" J. Controlled Release vol. 1 pp. 301-315, 1985.

Vega et al. "*Targeting Ariamycin to EGF Receptors by Site-Specific Conjugation of Monoclonal Antibody to Poly(L-Glutamic Acid)*". Division of Diagnostic Imaging and Department of Experimental Therapeutics, U.T.M.D. Anderson Cancer Center, 1515 Holcombe Blvd., Houston Texas, USA, no date.

Vega et al. "*Targeting Doxorubicin to EGF Receptors by Site-Specific Conjugation of C225 to Poly(L-Glutamic Acid) Through a Polyethylene Glycol Spacer*" Bioconjugate Chemistry vol. 826 pp. 832, 2002.

Vyas et al. "*Phosphatase-Activated prodrugs of Paclitaxel*" Taxane Anticancer Agents: Basic Science and Current Status, American Chemical Society, Washington, DC pp. 124-137, 1995.

Wahl "*Monoclonal Antibodies in Nuclear Medicine*" Nuclear Medicine Annual 1992, New York, Raven Press Ltd. pp. 91-103, 1992.

Wahl et al. "*Loss of Normal p53 Function Conferes Sensitation to Taxol by Increasing $G_2/M$ Arrest and Apoptosis*" Nat. Med. vol. 2(1) pp. 72-79, 1996.

Weiss et al. "*Hypersensitivity Reaction from Taxol*" J. Clin. Oncol. vol. 8(7) pp. 1263-1268, 1990.

Wen et al. "*Conjugation with $^{111}$In-DTPA-Poly(Ethylene Glycol) Improves Imaging of Anti-EGF Receptor Antibody C225*" J. Nuclear Medicine vol. 42 No. 10 pp. 1530-1537, 2001.

Wen et al. "*Improved Radiolabeling of PEGylated Protein: PEGylated Annexin V for Noninvasive Imaging of Tumor Apoptosis*" Bioconjugate Chemistry, 23 Pages, Feb. 21, 2002.

Wen et al. "Poly(ethylene glucol) Conjugated Anti-EGF Receptor Antibody C225 with Radiometal Chelator Attached to the Termini of Polymer Chains" Bioconjugate Chem. vol. 12 pp. 545-553, 2001.

Wu et al. "*Apoptosis Induced by an Anti-Epidermal Growth Factor Receptor Monoclonal Antibody in a Human Colorectal Carcinoma Cell Line and its Delay by Insulin*" J. Clin Invest. vol. 95 pp. 1897-1905, 1995.

Wu et al. "*imaging of Apoptosis with In-111 Labeled PEGylated Annexin V Abstract, AACR Conference*" Molecular Imaging in Cancer: Linking Biology, Function and Clinical Applications In Vivo vol. 1 p. 114, 2002.

Yasui et al. "*Expression of Epidermal Growth Factor Receptor in Human Gastric and Colonic Carcinomas*" Cancer Res vol. 48 pp. 137-141, 1995.

Yokoyama et al. "*Polymer Micelles as Novel Drug Carrier: Adriamycin-Conjugated Poly(ethylene glycol)-Poly(aspartic acid) Block Copolymer*" J. Controlled Release vol. 11 pp. 269-278, 1990.

Yokoyama et al. "*Preparation of Micelle-Forming Polymer-Drug conjugates*" Bioconjugate Chem. vol. 3 pp. 295-301, 1992.

Young et al. "*Influence of Immunoglobulin Heavy and Light-Chain Expression on B-Cell Differentiation*" Genes & Development vol. 8 pp. 1043-1057, 1994.

Abrams, et al. "*Technetium-99m-Human Polyclonal IgG Radiolabeled via the Hydrazino Nicotinamide Derivative for Imaging Focal Sites of Infection in Rats*", J. Nucl. Med., 31:2022-2028, 1990.

Alper et al. "Assessment of Renal Functional Changes Following Transurethral Prostatectomy Using Tc-99m ethylenedicysteine", J. Nuclear Med., 37:289P, Abstract No. 1292, 1996.

Anderson et al. "N,N'-Ethylene-di-L-Cysteine (EC) Complexes of Ga(III) and In(III): Molecular Modeling, Thermodynamic Stability and In Vivo Studies", Nucl. Med. Biol., 22:165-173, 1995.

Antony, Asak C., Folate Receptors, Annu. Rev. Natr., vol. 16, pp. 501-521, 1996.

Baidoo and Lever, "Evaluation of a diaminedithiol-based bifunctional chelate for labeling small molecules with 99m Tc", Technetium and Rhenium in Chemistry and Nuclear Medicine, p. 369-374, 1990.

Baidoo et al., "Synthesis of a New Diaminedithol Bifunctional Chelate for the Preparation of Neutral Technetium Complexes", J. Nucl. Med., 31:806, Abstract No. 414, 1990.

Bakker et al., "Receptor Scintigraphy with a Radioiodinated Somatostatin Analogue: Radiolabeling, Purification, Biologic Activity, and In Vio Application in Animals", J. Nucl. Med., 31:1501-1509, 1990.

Becker, et al., Short Communication: Analysis of E.-Cadherin in Diffuse-Type Gastric Cancer Using Mutation-specific Monoclonal Antibody, American Journal of Pathology, vol. 155, No. 6, pp. 1803-1809, 1999.

Blondeau et al., "Dimerization of an intermediate during the sodium in liquid ammonia reduction of L-thiazolidine-4-carboxylic acid", Can J. Chem, 45:49-52, 1967.

Brogi, et al., Hypoxia-induced Paracrine Regulation of Vascular Endothelial Groth Factor Receptor Expression, J. Clin. Invest., vol. 97, No. 2, pp. 469-476, 1996.

Budihardjo, et al., Biochemical Pathways of Caspase Activation During Apoptosis, Annu. Rev. Cell. Dev. Biol., vol. 15 pp. 269-290, 1999.

Burgen, A.S.V., Targets of Drug Action, Annu. Rev. Pharmacol. Toxicol., vol. 40, pp. 1-16, 2000.

Bush, et al., "Definitive Evidence for Hypoxic Cells Influencing Cure in Cancer Therapy", Br J Cancer, (Suppl.mIII) 37:302-306, 1978.

Campbell et al., "Folate-binding Protein Is a Marker for Ovarian Cancer", Cancer Res, 51:5329-5338, 1991.

Chen et al., "Biological and Pharmacokinetic Evaluation of Tc-99m Ma2G2-b:A Potential Renal Agent", J. Nuclear Med., 35:263P, Abstract No. 1082, 1994.

Cherif et al., "Rapid Synthesis of 3-[18F ] Fluoro-1-(2'-Nitro-1'-Imidazolyl)-2-Propanol) [18F] Fluoromisonidazole)", Pharm Res., 11:466-469, 1994.

Cleynhens et al., "Synthesis and Biological Evaluation in Mice of A Monoamide Derivative of Tc-99m-L, L-EC", J. Nuclear Med., 38:186P, Abstract No. 799, 1997.

Coney et al., "Chimeric Murine-Human Antibodies Dircted against Folate Binding Receptor Are Efficiant Mediators of Ovarian Carcinoma Cell Killing", Cancer Res., 54:2448-2455, 1994.

Corlija et al., "Contribution of Radiolytically Induced Dissociation of 99m-Tc-d, 1-HMPAO in Aqueous Solutions", J. Nuclear Med., 31:806, Abstract No. 413, 1990.

Craig et al., "Renal Outcomes for Children One Year After Urinary Tract Infection", J. Nuclear Med., 37:46P, Abstract No. 175, 1996.

Dagli et al., "Analysis of the Complete Dynamic Scan Data for Camera-Based Determination of Renal Function", Nuclear Med., 37:91P, Abstract No. 354, 1996.

Davidson et al., "A new Class of Oxotechnetium (5+) Chelate Complexes Containing a $TcON_2S_2$ Core", Inorg Chem, 20:1629-1632, 1981.

de Klerk et al., "Aspirin Versus Captopril Renography in the Diagnosis of Renal Artery Stenosis", J. Nuclear Med., 37:289P, Abstract No. 1291, 1996.

Dewanjee et al, "Labeling Sntisense Oligodeoxynucleotide (on) with TC-99m and Hybridization with c-myc Oncogene mrna in P388 Leukemic Cells", J. Nuclear Med., 35:263P, Abstract No. 1081, 1994.

Dezutter et al., "Preparation and Biological Evaluation of Technetium-99m-L, L-propylenedicsteine", J. of Labelled Cpd. Radiopharm., 42:553-565, 1999.

Dische, "A Review of Hypoxic Cell Radiosensitization", Int J Radiat Oncol Biol Phys, 20: 147-152, 1991.

Eisenhut et al., "Synthesis and In Vivo Testing of a Bromobutyl Substituted 1,2-Dithia-5,9-diazacycloundecane: a Versatile Precursor for New $^{99m}TC$-Bis(aminoethanethiol) Complexes", Nucl. Med. Biol., 16: 805-811, 1989.

Eshima et al., "Evaluating the Role of Protein Binding on the Renal Extraction of Tc-99m Tubular Agents Utilizing an Isolated Perfused Rate Kidney Model", J. Nuclear Med., 37:47P, Abstract No. 178, 1996.

Fanciulli et al., "Glycolysis and Growth Rate in Normal and in Hexokinase-Transfected NIH-3T3 Cells", Oncology Res., 6:405-409, 1994.

Frankel, et al., Targeted Toxins, Clinical Cancer Research, vol. 6, pp. 326-334, 2000.

Franklin et al., "New Anti-Lung-Cancer Antibody Cluster 12 Reacts with Human Folate Receptors Present on Adenocarcinoma" Int. J. Cancer-Supplement, 8:89-95, 1994.

Garayoa, et al., Hypoxia-Inducible Factor-1 (HIF01) Up-Regulates Adrenomedullin Expression in Human Tumor Cell Lines during Oxygen Deprivation: A Possible Promotion mechanism of Carcingogenesis, Molecular Endocrinology, vol. 14, No. 6, pp. 848-862, 2000.

Girard, et al., Mechanisms by Which Carbohydrates Regulate Expression of Genes for Glycolytic and Lipogenic Enzymes, Annu. Rev. Nuir, vol. 17, pp. 325-352, 1997.

Giraud et al. "Application to a Cartilage Targeting Strategy: Synthesis and in Vivo Biodistribution of $^{14}C$-Labeled Quaternary Ammonium-Glucosamine Conjugates", Bioconjug. Chem., 11:212-218, 2000.

Goh et al., "Growth Hormone Promotion of Tubulin Polymerization Stabilizes the Microtubule Network and Protects Against Colchicine-Induced Apoptosis" Endocrinology, 139:4364-4372, 1998.

Goldsmith et al., Receptor Imaging: Competitive or Complementary to Antibody Imaging? Seminars in Nucl. Med., vol. 27, No. 2, pp. 85-93, 1997.

Goldsmith et al., "Somatostatin-Receptor Imaging in Lymphoma" Sem. Nucl. Med., 25:262-271, 1995.

Guozheng and Boli, "A New Potential Renal Imaging Agent $^{99M}TcN$-EC", J. Labelled Compounds and Radiopharmaceuticals, 37:797-798, 1995.

Hadley et al., "Magnetic Resonance Imaging in Acute Head Injury", Clin. Rad., 39:131-139, 1988.

Harada et al., "Insulin-induced egr-1 Expression in Chinese Hamster Ovary Cells Is Insulin Receptor and Insulin Receptor Substrate-1 Phosphorylation-independent" J. Biol. Chem., 270:26632-26638, 1995.

Hay et al., "Hypoxia-Selective Antitumor Agents. 8. Bis(nitroimidazolyl)alkanecarboxamides: A New Class of Hypoxia-Selective Cytotoxins and Hypoxic Cell radiosensitisers", J. Med. Chem., 37:381-391, 1994.

Hermann and Patel, "Adaptive Recognition by Nucleic Acid Aptamers" Science, 287:820-825, 2000.

Hibi, et al., PGP9.5 as a Candidate Tumor Marker for Non-Small-Cell Lung Cancer, American Journal of Pathology, vol. 155, No. 3, pp. 711-715, 1999.

Holm et al., "Folate Receptor of Human Mammary Adenocarcinoma" APMIS, 102:413-419, 1994.

Hsueh and Dolnick, "Altered Folate-Binding Protein mRNA Stability in KB Cells Grown in Folate-Deficient Medium" Biochem., Pharmacol, 45:2537-2545, 1993.

Ilgan et al., "$^{99m}Tc$-Ethylenedicysteine-Folate: A New Tumor Imaging Agent. Synthesis, Labeling and Evaluation in Animals" Caner Biotherapy & Radiopharmaceuticals, 13:427-435, 1998.

Itoh et al., "Graphic (Patlak) Method in $Tc$-$^{99m}$-MAG3 Renal Scrintigraphy: Noninvasive Calculation of Extraction Fraction (EF) and Renal Plasma Flow (RPF)", J. Nuclear Med., 37:291P, Abstract No. 1300, 1996.

Jamar et al., "Clearance of the New Tubular Agent $TC$-$^{99m}$-L,L-ETHY-Lenedicsteine: Estimation by a Simplified Method" J. Nucl. Med., 34:129P, Abstract No. 516, 1993.

Jamar et al., *Clinical Evaluation of TC-99m,L,L-Ethylenedicysteine, a New Renal Tracer, in transplanted Patients* J. Nucl. Med., 34:129p, Abstract No. 514, 1993.

John et al., "*TC-$^{99m}$ Labeled Ethylenediamines: Quest for Sigma Receptor Chelates*" J. Nucl. Med., 38:186P, Abstract No. 798, 1997.

Jones and Mayer "*Glucose Metabolism in the Rat Small Intestine: the Effect of Glucose Analogues on Hexokinase Activity*" Biochem. J, 132:125-128, 1973.

Kabasakal "*Technetium-99m ethylene dicysteine: a new renal tubular function agent*" Eur. J. Nucl. Med., 27:351-357, 2000.

Kabasakal et al. "*Clinical Comparison of Thechnetium-$^{99m}$-EC, Technetium-$^{99m}$-MAG3 and Iodine-131-OIH in Renal Disorders*" J. Nucl. Med., 36:224-228, 1995.

Kabasakal et al. "*Evaluation of Technetium-$^{99m}$-Ethylenedicysteine in Renal Disorders and Determination of Extraction Ratio*" J. Nucl. Med., 36:1398-1403, 1995.

Kabasakal et al. "*Prospective Validation of Single Plasma Sample $^{99m}$Tc-Ethylenedicysteine Clearance in Adults*" J. Nucl. Med., 40:429-431, 1999.

Kabasakal et al. "*Simplified Technetium-99m-EC Clearance in Adults from a Single Plasma Sample*" J. Nucl. Med., 38:1784-1786, 1997.

Kanazawa, et al., *$^{19}F$ NMR of 2-Deoxy-2-fluoro-D-glucose for Tumor Diagnosis in Mice. An NDP-Bound Hexose Analog as a New NMR Target for Imaging*, NMR in Biomedicine, vol. 10, pp. 35-41, 1997.

Kanvinde et al. "Technetium-99m-y-pyrones: a new class of tc-99m cationic complexes" J. Nucl. Med., 31:908, Abstract No. 866, 1990.

Kao et al. "Role of Radioisotope Penile Plethysmography in the Evaluation of Penile Hemodynamic of Impotent Patients" J. Nucl. Med., 37:292P, Abstract No. 1304, 1996.

Kao, et al., *Detection of Esophageal Carcinoma Using Tc-99m MIBI SPECT Imaging*, Clinical Nuclear Medicine, vol. 19, No. 12, pp. 1069-1074, 1994.

Kato, et al., *Targeted Delivery of Peptides, Proteins, and Genes by Receptor-Mediated Endocytosis*, Critical Reviews in Therapeutic Drug Carrier Systems, vol. 14, No. 3, pp. 287-331, 1997.

Kengen "*Good Results of Tc-99m-MAG3 Clearance Measurements with a Dual Headed Gamma Camera without Plasma Samples*" J. Nucl. Med., 37:91P, Abstract No. 353, 1996.

Kikukawa et al. "*Early and delayed Tc-99m ECD brain SPECT in SLE patients with CNS involvement*" Annals of Nucl. Med., 14:25-32, 2000.

Kim et al. "Synthesis, biodistribution and imaging of mammary tumors using $^{99m}$Tc-EC-Polyglutamate: a glutamate receptor peptide" J. Nucl. Med., 41:231P, Abstract No. 1027, 2000.

King, et al., *Imaging of bone infection with labelled white blood cells: role of contemporaneous bone marrow imaging*, European Journal of Nuclear Medicine, pp. 148-151, 1990.

Knight, et al., *Radiolabeling of Fibrinogen Using the Lodogen Technique*, Thromb Haemostas (Stuttgart), vol. 46, No. 3, pp. 593-596, 1981.

Knight, L. et al., "*Thrombus Imaging with Technetium-99m Synthetic Peptides Based upon the Binding Domain of a Monoclonal Antibody to Activated Platelets*" The Journal of Nuclear Medicine vol. 35:282-288, 1994.

Koh, Wui-Jin, et al., *Imaging of Hypoxia in Human Tumors with [F-18]Fluoromisonidazole*, Int. J. Radiation Oncology Biol. Phys. vol. 22 pp. 199-212, 1991.

Kranz, D., et al. *Conjugates of folate and anti-T-cell-receptor antibodies specifically target folate-receptor-positive tumor cells for llysis*, Proc. Natl. Acad. Sci. USA, vol. 92, pp. 9057-9061, 1995.

Lamberts, S.W.J., et al., *Somatostatin Receptor Imaging, In Vivo Localization of Tumors with a Radiolabeled Somatostatin Analog*, J. Steroid Biochem. Molec. Biol., vol. 37, No. 6 pp. 1079-1082, 1990.

Leamon, C., et al., *Cytotoxicity of Folate-Pseudomonas Exotoxin Conjugates Toward Tumor Cells*, The Journal of Biological Chemistry, vol. 268, No. 33, pp. 24847-24854, 1993.

Leamon, C., et al., *Cytotoxicity of Momordin-Folate Conjugates in Cultured Human Cells*, The Journal of Biological Chemistry, vol. 267, pp. 24966-24971, 1992.

Leamon, C., et al., *Delivery of macromolecules into living cells: A method that exploits folate receptor endocytosis*, Proc. Natl. Acad. Sci. USA, vol. 88, pp. 5572-5576, 1991.

Lee, R., et al., *Delivery of Liposomes into Cultured KB Cells via Folate Receptor-mediated Endocytosis*, Journal of Biological Chemistry, vol. 269:3198-3204, 1994.

Liang, et al., *The Use of Diaminodithiol for Labeling Small Molecules with Technetium-99m*, Nucl. Med. Biol, vol. 14, No. 1, pp. 63-67, 1987.

Lu, Matthias C., *Antimiotic Agents*, American Chemical Society, ACS Profession Reference: *Cancer Chemotherapeutic Agents*, Chapter 9 pp. 345-368, 1995.

Mang'era, et al., *Synthesis and Evaluation of B-Homocysteine Derivatives of $^{99m}$Tc L,L-EC and $^{99m}$Tc-L,L-ECD*, J. Labelled Cpd. Radiopharm. 42, pp. 683-699, 1999.

Marti, et al., *Systemic hypoxia changes the organ-specific distribution of vascular endothelial growth factor and its receptors*, Proc. Natl. Acad. Sci. USA, vol. 95, pp. 15809-15814, 1998.

Martin, Gary, et al., *Enhanced Binding of the Hypoxic Cell Marker [$^{3}$]Fluoromisoniadazole in Ischemic Myocardium*, J Nucl Med 30, pp. 194-201, 1989.

Mason, et al., *99mTc-Desferoxamine: Production, Stability and solute Clearance Measurements After Aerosolization*, The Journal of Nuclear Medicine, Proceedings of the 37th Annual Meeting, p. 908, Abstract No. 865, 1990.

Mather, et al., *Tumour Cell Uptake of Technetium Dithiocarbmate Complexes*, The Journal of Nuclear Medicine, vol. 38, No. 5 (Supplement), p. 186, Abstract No. 797, 1997.

Mathias, et al. "Indium-111-DTPA-Folate as a Radiopharmaceutical for Targeting Tumor-Associated Folate binding protein (FBP)" J. Nucl. Med., 38:133P, Abstract No. 500, 1997.

Mathias, et al. "*Sysnthesis of Tc-99m-DTPA Folate and Preliminary Evaluation as a Folat-Receptor-Targeted Readiopharmaceutical*" J. Nucl. Med., (Supplemental); 38:87P, Abstract No. 320, 1997.

Mathias, et al., *Tumor-Selective Radiopharmaceutical Targeting via Receptor-Mediated Endocytosis of Gallium-67-Deferoxamine-Folate*, J. Nucl. Med. vol. 37:1003-1008, 1995.

Michiels, et al., *Simultaneous Estimation of Effective Renal Plasma Flow and Glomerular Filtration Rate Using Tc-99m-EC*, The Journal of Nuclear Medicine vol. 73:91P, Abstract No. 355, 1996.

Mochizuki, et al. "*Synthesis of poly-L-glotamates containing 5-substituted uracil moieties*" Nucleic Acids Symp. Ser., 16:121-124, 1985.

Moller, et al., *Biologic Activities of Naturally Occuring Human Insulin Receptor Mutations*, The Journal of Biological Chemistry, vol. 266, No. 17, pp. 10995-11001, 1991.

Moran, Justin K., *Technetium-99m-EC and Other Potential New Agents in Renal Nuclear Medicine*, Seminars in Nuclear Medicine, vol. XXIX, No. 2, pp. 91-101, 1999.

Morton, et al., *Comparison of 2-point postural drainage with diuresis renography in the assessment hydronephrosis*, The Journal of Nuclear Medicine, vol. 37:46P, Abstract No. 174, 1996.

Mrhac, et al., *Abnormal First-Pass Flow through the Azygos Vein from Valsalva Maneuver*, Clinical Nucl. Med., 21:331-332, 1996.

Nosco, et al., *Development of a Kit Formulation for $^{99m}$TcMAG$_3$ of Very High Purity and Very High Stability*, The Journal of Nuclear Medicine, vol. 31, No. 5, pp. 907-908, 1990.

Offield, et al., *PDX-1 is required for pancreatic outgrowth and differentiation of the rostral duodenum*, Development 122, pp. 983-995, 1996.

Orr, et al., *Similarity of Folate Receptor Expression in UMSCC 38 Cells to Squamous Cell Carcinoma Differentiation Markers*, Journal of the National Cancer Institute, vol. 87, No. 4, pp. 299-303, 1995.

Ozker, et al., *Technetium-99m-N,N-Ethylenedicysteine—A Comparative Study of Renal Scintigraphy with Technetium-99m-MAG3 and Iodine-131-OIH in Patients with Obstructive Renal Disease*, The Journal of Nuclear Medicine, vol. 35, No. 5, pp. 840-845, 1994.

Piper, et al., *A Synthetic Approach to Poly(γ-glutamyl) Conjugates of Methotrexate*, J. Med. Chem., 26:291-294, 1983.

Pirmettis, et al., *Synthesis and Characterization of the TcD(EC) Complex, a Renal Imaging Agent*, Journal of Nuclear Medicine, vol. 35, No. 5, 263P, Abstract No. 1079, 1994.

Popovici, et al., *The Influence of Some Antibiotics on Hexokinase and Pyruvate-kinase Activity in the Rat Liver and Kidney*, Arch. int. Pharmacodyn. 193, pp. 80-86, 1971.

Pruvolich, et al., *Clinical Evaluation of Technetium-99m-L,L-Ethylenedicysteine in Patients with Chronic Renal Failure*, The Journal of Nuclear Medicine, vol. 38, No. 5, pp. 809-814, 1997.

Raffauf, et al., *Colchicine. Derivatives of Trimethylcolchicinic Acid*, Journal of the American Chemical Society, vol. 75, No. 21, pp. 5291-5294, 1953.

Rasey, et al., *Characteristics of the Binding of Labeled Fluoromisonidazole in Cells in Vitro*, Radiation Research, vol. 122, pp. 301-308, 1990.

Rasey, et al., *Radiolabeled Fluoromisonidazole as an Imaging Agent for Tumor Hypoxia*, I.J. Radiation, Oncology Biol. Phys., vol. 17, No. 5, pp. 985-991, 1989.

Ratner, et al., *The Action of Formaldehyde upon Cysteine*, The Journal of the American Chemical Society, vol. 59, pp. 200-206, 1937.

Rihova et al., *Receptor-mediated targeted drug or toxin delivery*, advanced drug delivery reviews, vol. 29, pp. 273-289, 1998.

Rogers, et al., *Neomycin Effects on Glucose Transport by Rat Small Intestine*, Digestion 1, pp. 159-164, 1968.

Ross, et al., *Differential Regulation of Folate Receptor Isoforms in Normal and Malignant Tissues In Vivo and in Established Cell Lines*, Cancer, 73:2432-2443, 1994.

Sasaki, et al. *Assessment of Antioxidative Ability in Brain: Imaging of Glutathione Localization with Technetium-99M Meso-Hesamethyl Propyleneamine Oxime*, Journal of Nuclear Medicine, vol. 35, No. 5, 263P-264P, Abstract No. 1083, 1994.

Sato, et al., *Simple Estimation of Fractional Renal Uptake of Tc-99m MAG3 Using Graphical Analysis Without Syringe Counting and Renal Depth Correction*, Journal of Nuclear Medicine, vol. 37, No. 5, 292P, Abstract No. 1303, 1996.

Schepdael, et al. *Capillary electrophoretic analysis of ethylene dicysteine, a precursor of the radiopharmaceutical $^{99m}Tc$ ethylene dicysteine*, Journal of Chromatography B, vol. 697, pp. 251-254, 1997.

Seabold, et al., *Comparison of $^{99m}Tc$-Methoxyisobutyl Isonitrile and $^{201}Tl$ Scintigraphy for Detection of Residual Thyroid Cancer After $^{131}I$ Ablative Therapy*, The Journal of Nuclear Medicine, vol. 40, No. 9, pp. 1434-1440, 1999.

Semenza, Gregg L., *Regulation of Mammalian $O_2$ Homeostasis by Hypoxia-InducibleFactor 1*, Annu. Rev. Cell Dev. Biol., vol. 15, pp. 551-578, 1999.

Shankar, et al., *Glucosamine Infusion in Rats Mimics the B-Cell Dysfunction of Non-Insulin-Dependent Diabetes Mellitus*, Metabolism, vol. 47, pp. 573-577, 1998.

Shattuck, et al., *Validation of the Two Sample Technique for Measuring GFR, in Renal Transplant Patients*, Journal of Nuclear Medicine, vol. 36, No. 5, 231P, Abstract No. 1036, 1995.

Shuke, et al., *Modified Renal Counting Method for Estimation of Tc-99m MAG3 Renal Clearance*, Journal of Nuclear Medicine, vol. 37, No. 5, 291P, Abstract No. 1301, 1996.

Skzypezak-Jankun, et al., *Structure of the Hirugen and Hirulog 1 Complexes of x-Thrombin*, J. Med. Biol. vol. 221, pp. 1379-1393, 1991.

Stoffel, et al., *Evaluation of Technetium-99m-L,L-EC in Renal Transplant Recipients: A Comparative Study with Technetium-99m-MAG3 and Iodine-125-OIH*, J. Nucl Med, vol. 35, No. 12, pp. 1951-1958, 1958.

Subramanisa, et al., *Transchelation Reactions in Labeling ECD with Tc-99m*, The Journal of Nuclear Medicine, vol. 31, No. 5, pp. 908-909, Abstract No. 867, 1990.

Sudimack, et al., *Targeted drug delivery via the folate receptor*, advanced drug delivery reviews, vol. 41, pp. 147-162, 2000.

Sun, et al., *Indium (III) and Gallium (III) Complexes of Bis(aminoethanethiol) Ligands with Different Denticities: Stabilities, Molecular Modeling, and in Vivo Behavior*, J. Med. Chem., vol. 39, pp. 458-470, 1996.

Surma, et al., *Usefulness of $^{99}TC^m$-N,N'-ethylene-1-dicsteine complex for dynamic kidney investigations*, Nuclear Medicine Communications, vol. 15, pp. 628-635, 1994.

Suzuki et al. "A modified graphic method for estimation of glomerular filtration index using dynamic renal images with Tc-99m DTPA" J. Nucl. Med., 36:231P, Abstract No. 1035, 1995.

Tait, et al., *Site-Specific Mutagenesis of Annexin V: Role of Residues from Arg-200 to Lys-207 in Phospholipid Binding[1]*, Archives of Biochemistry and Biophysics, vol. 288, No. 1, pp. 141-144, 1991.

Takamizawa, et al., *Differential Apoptosis Gene Expression in Pediatric Tumors of the Kidney*, Journal of Pediatric Surgery, vol. 35, No. 2, pp. 390-395, 2000.

Taylor, et al., *comparison of Tc-99mo(N,N$^1$-Ethylenedicsteine Isomers in Rats and in Normal Volunteers*, The Journal of Nuclear Medicine, vol. 37, No. 5, 46P-47P, 1996.

Taylor, et al., *Comparison of Technetium-99m-LL-EC Isomers in Rats and Humans*, The Journal of Nuclear Medicine, vol. 38, No. 5, pp. 821-826, 1997.

Tsukamoto, et al., *The Quntitation of Absolute Tc-99m-DMSA Renal Uptake in Children from Planar Posterior-View Method*, Journal of Nuclear Medicine, vol. 37, No. 5, 291P, Abstract No. 1299, 1996.

Tubis, et al., *The Preparation of $^{99m}$Technetium-Labeled Cystine, Methionine and a Synthetic Polypeptide and their Distribution in Mice*, International Journal of Applied Relation and Isotopes, vol. 19, pp. 835-840, 1968.

Tuli, et al., *Comparison of a Simplified Quanitation of Tc-99m MAG-3Renogram to Core Needle Biopsy in the Diagnosis of Renal Transplant Rejection*, Journal of Nuclear Medicine, vol. 37, No. 5, 289P, Abstract No. 1290, 1996.

Ugur, et al., *Renovascular Hypertension due to Takayasu's Arteritis Demonstrated by Tc-99m Ethylenedicysteine Captopril Scintigraphy*, Clinical Nuclear Medicine, vol. 21, No. 9, pp. 714-716, 1996.

Ugur, et al., *Technetium-99m-Ethylenedicysteine in the Diagnosis and Follow-Up of Renovascular Hypertension*, Investigative Radiology, vol. 31, No. 6, pp. 379-381, 1996.

Ugur, et al., *Technetium-99m-Ethylenedicysteine: An Alternative Agent to Detect Renovascular Hypertension*, The Journal of Nuclear Medicine, vol. 38, No. 10, pp. 1662-1664, 1997.

Ugur, et al., *The Diagnosis of Renovascular Hypertension with Tc-iim Ethylenedicysteine Captopril Scintigraphy*, Journal of Nuclear Medicine, vol. 37, No. 5, 291P-292P. Abstract No. 1302, 1996.

Ugur, et al., *The Diagnosis of Renovascular Hypertension with Technetium-99m-Ethylenedicysteine Captopril Scintigraphy*, Investigative Radiology, vol. 31, No. 8, pp. 497-501, 1996.

Valk, et al., *Hypoxia in Humans Gliomas; Demonstration by PET with Fluorine-18-Fluoromisonidazole*, J. Nucl Med vol. 333, pp. 2133-2137, 1992.

Van Nerom, et al., Comparative Evaluation of Tc-99m L,L-Ethylenedicysteine and Tc-99m MAG3 in Volunteers, Eur J Nucl. Med., p. 417, Abstract No. 105, 1990.

Van Nerom, et al., *Comparison of Renal Excretion Characteristics of Isomers L,L and D.D of Tc-99m Ethylenedicysteine*, J. Nucl. Med., 31:806p, Abstract No. 412, 1990.

Van Nerom, et al., *First experience in healthy volunteers with technetium-99m L,L-ethylenedicysteine, a new renal imaging agent*, European Journal of Nuclear Medicine, vol. 20, No. 9, pp. 738-746, 1993.

Van Nerom, et al., *Optimalization of the Labelling of Ethylenedicysteine (EC) with Technetium-99m*, Journal of Labelled Compounds and Radiopharmaceuticals, vol. XXX, pp. 37-39, 1991.

Verbruggen "Evaluation of Tc-99m L, L-Ethylenedicysteine as a Potential Alternative to Tc-99m MAG 3" Eur. J. Nucl. Med., 16:429, Abstract No. 156, 1990.

Verbruggen, et al., *Is Syn or Anti Orientation of the Oxotechnetium and Carboxyl Group In Tc-99m Renal Function Agents Affecting the Renal Excretion Rate?*, Journal of Labelled Compounds and Radiopharmaceuticals, vol. XXX, pp. 86-88, 1991.

Verbruggen, et al., *Tc-99m L,L-Ethylenedicysteine, a Potential Alternative to Tc-99m MAG3*, The Journal of Nuclear Medicine, vol. 31, No. 5, p. 908, Abstract No. 864, 1990.

Verbruggen, et al., *Technetium-99m-L,L-Ethylenedicysteine: A Renal Imaging Agent. I. Labeling and Evaluation in Animals*, J. Nucl Med, vol. 33, pp. 551-557, 1992.

Villevalois-Cam, et al., *Insulin-Induced Redistribution of the Insulin-Like Growth Factor II/Mannose 6-Phosphate Receptor in Intact Rat Liver*, Journal of Cellular Biochemistry, vol. 77, pp. 310-322, 2000.

Walsh, et al., *Noninvasive Estimation of Regional Myocardial Oxygen Comsumption by Positron Emission Tomography with Carbon-II Acetate in Patients with Myocardial Infarction*, J. Nuclear Medicine, vol. 30, No. 11, pp. 1798-1808, 1989.

Wang, et al., *Design and Synthesis of [$^{111}$In]DTPA-Folate for Use as a Tumor-Targeted Radiopharmaceutical*, Bioconjugate Chem. vol. 8, pp. 673-679, 1997.

Wang, et al., *Synthesis, Purification, and Tumor Cell Uptake of $^{67}$Ga-Deferoxamine-Folate, a Potential Radiopharmaceutical for Tumor Imaging*, Bioconjugate Chem., vol. 7, pp. 56-62, 1996.

Washburn, et al., *Reliable Kit Preparation of Tc-99m Pentavalent Dimercaptosuccinic Acid [Tc-99m (V) DMSA].*, Journal of Nuclear Medicine, vol. 35, No. 5, 263P, Abstract No. 1080, 1994.

Weir, et al., *Prognostic value of single-photon emission tomography in acute ischaemic stroke*, European Journal of Nuclear Medicine, vol. 24, No. 1, pp. 21-26, 1997.

Weitman, et al., *Cellular Localization of the Folate Receptor: Potential Role in Drug Toxicity and Folate Homeostasis[1]*, Cancer Research, vol. 52, pp. 6708-6711, 1992.

Weitman, et al., *Distribution of the Folate Receptor GP38 in Normal and Malignant Cell Lines and Tissues[1]*, Cancer Research, vol. 52, pp. 3396-3401, 1992.

Weitman, et al., *The folate receptor in central nervous system malignancies of childhood*, Journal of Neuro-Oncology, vol. 21, pp. 107-112, 1994.

Wells, et al., *Glycosylation of Nucleocytoplasmic Proteins: Signal Transduction and O-GlcNAc*, Science Magazine, vol. 291, pp. 2376-2378, 2001.

Westerhof, et al., *Membrane Transport of Natural Folates and Antifolate Compounds in Murine L1210 Leukemia Cells: Role of Carrier- and Receptor-mediated Transport Systems[1]*, Cancer Research, 51:5507-5513, 1991.

Yamori, et al., *Potent Antitumor Activity of MS-247, a Novel DNA Minor Groove Binder, Evaluated by an* in Vitro *and* in Vivo *Human Cancer Cell Line Panel[1]*. Cancer Research, vol. 59, pp. 4042-4049, 1999.

Yang et al., *Imaging tumor folate receptors using $^{99m}$Tc-Ethylenedicysteine-folate*, Proceedings of the American Assoc. for Cancer Research, 40:259, Abstract No. 1720, 1999.

Yang, et al., *$^{99M}$Tc-EC-Deoxyglucose: Synthesis, Cellular Uptake, Biodistribution and Scintigraphic Imaging*, J. Labelled Cpd. Radiopharm. vol. 44, Suppl. 1, pp. 258-259, 2001.

Yang, et al., *Development of F-18—labeled Fluoroerythronitroimidazole as a PET Agent for Imaging Tumor Hypoxia[1]*, Nuclear Medicine, Radiology, vol. 194, No. 3, pp. 795-800, 1995.

Yang, et al., *Imaging Tumor Folate Receptors Using Radiolabeled Folate and Methotrexate*, J. Labelled Cpd. Radiopharm., vol. 42, Suppl. 1, pp. 5696-5697, 1999.

Yang, et al., *Molecular Imaging Using $^{99M}$TC-EC-Nitroimidazole, and $^{99M}$TC-EC-Annexin V in Tumor-Bearing Rodents*, Proceedings of the American Association for Cancer Research Annual Meeting, 41:766, Abstract No. 4865, 2000.

Yang, et al., *Noninvasive Assessment of Tumor Hypoxia with $^{99M}$Tc Labeled Metronidazole*, Pharmaceutical Research, Vo. 16, No. 5, pp. 743-750, 1999.

Yoshino, et al. *Differential Effects of Troglitazone and D-Chiroinositol on Glucosamine-Induced Insulin Resistance* in Vivo *in Rats*, Metabolism, vol. 48, No. 11, pp. 1418-1432, 1999.

Zakko, et al., *Biliary Excretion of Tc-99m EC in Renal Studies*, Clinical Nuclear Medicine, Vo. 23, No. 7, pp. 417-419, 1998.

Zarencyrizi, et al., *Synthesis of [$^{99m}$Tc]ethylenedicysteine-colchicine for evaluation of antiangiogenic effect*, Anti-Cancer Drugs, vol. 10, pp. 685-692, 1999.

EP International Search Report; PCT/US0212502; 5 Pgs., Mailed Apr. 6, 2006.

Ke Shi et al.; "Site-specific Conjugation of Monoclonal Antibody to Polyethylene Glycol-poly(L-glutamic acid) (PEG-PG) Copolymer for Targeted Drug Delivery"; Proceedings of the American Association for Cancer Research Annual Meeting, vol. 43; 1 Pg., Mar. 2002.

Wu Qingping et al; "Antitumor Activity of Doxorubicin (Dox)-bound Polyethylene Glycol-poly(L-glutamic Acid) (PEG-PG) Block Copolymer with Amide and Ester Linkages"; Proceedings of the American Association for Cancer Research Annual Meeting, vol. 44, 1 Pg., Jul. 2003.

Supplementary Partial European Search Report; PCT/US0212510; pp. 5, Mailed Apr. 26, 2006.

A. Kurihara et al.; "Epidermal Growth Factor Radiopharmaceuticals: $^{111}$In Chelation, Conjugation to a blood-Brain Barrier Delivery Vector via a Biotin-Polyethylene Linker, Pharacokinetics, and in Vivo Imaging of Experimental Brain Tumors"; Bioconjugate Chem., vol. 10, No. 3; pp. 502-511, 1999.

F.G. Blankenberg et al.; "In vivo Detection and Imaging of Phosphatidylserine Expression During Programmed Cell Death"; Proc. Natl. Acad. Sci., vol. 95; pp. 6349-6354, 1998.

A. Abuchowski et al.; "Effect of Covelant Attachment of Polyethylene Glycol on Immunogenicity and Circulating Life of Bovine Liver Catalase"; Journal of Biological Chemistry, vol. 252, No. 11, pp. 3582-3586, Jun. 10, 1977.

G. DeSantis et al.; "Chemical Modifications of Enzymes for Enhanced Functionality"; Curr. Opin. Biotechnol., 10(4), pp. 324-330, 1999.

C. Liu et al.; "Eradication of Large Colon Tumor Xenografts by Targeted Delivery of Maytansinoids"; Proc. Natl. Acad. Sci. USA, vol. 93, pp. 8618-8623, 1996.

PCT Notification of Transmittal of International Preliminary Examination Report for International Application No. PCT/US02/12510, 5 pages, Mailed May 12, 2005.

\* cited by examiner

DENDRITIC POLY (AMINO ACID) CARRIERS AND METHODS OF USE

PRIORITY CLAIM

This application claims priority under 35 U.S.C. §119(e) to U.S. Provisional Patent Application Ser. No. 60/342,807, filed Dec. 21, 2001, entitled "Dendritic Poly(Amino Acid) Carriers".

STATEMENT OF GOVERNMENT INTEREST

The present invention was developed under a grant from the National Institutes of Health/National Cancer Institute grant No. CA74819. The U.S. Government may have certain rights to the invention.

FIELD OF THE INVENTION

The present invention relates generally to the field of drug delivery systems. More particularly, it concerns formulations for in vivo delivery of therapeutic and diagnostic agents. The present invention also concerns methods of preparation of such delivery systems and methods for employing such delivery systems to deliver drugs, diagnostic agents, and other therapeutic agents to target areas.

BACKGROUND OF THE INVENTION

The success of certain types of treatments, such as cancer chemotherapy or gene therapy, is largely dependent on the development of delivery systems or carriers that may selectively and efficiently deliver a drug, other therapeutic agent, or diagnostic agent to target regions, such as organelles, cells, organs, tissues, or organisms with minimal delivery or toxicity to non-target areas. This is because these treatments are ultimately limited by the toxicity or the danger of the treating substance to normal, or non-targeted sites, organelles, cells, organs, or tissues. Therefore, targeted agent delivery may theoretically allow the use of a reduced dose to achieve the same therapeutic response, with a consequent decrease in systemic toxicity. It also should allow more effective and less dangerous uses of normal or increased doses. The need for efficient carriers is especially apparent in the area of cancer treatment because the majority of anticancer drugs have a detrimental effect on normal cells. In the past, several carriers based on polymers have been developed, but design improvements are needed.

There are several factors that contribute to maximum targeted agent (e.g., drug, other therapeutic agent, or diagnostic agent) delivery: (1) a system which allows efficient loading and retention of a selected agent; (2) minimization of the blood clearance of the conjugate in comparison with the rate of extravasation in the target region; (3) preservation of accessible antigen binding sites with enhancement of the binding affinity; and (4) use of a degradable and biocompatible polymer. In addition to the above factors, the macromolecule used is of importance because shape, flexibility of the polymer, and charge influence penetration and receptor binding affinity (Drobnik & Rypacek, 1984). Increasing the size of the polymeric carrier above that of the glomerular filtration threshold, being approximately 45 Å in hydrodynamic radius, can substantially decrease the renal clearance rate (Petrak & Goddard, 1989). Polymers with sufficiently long circulation times may then exhibit efficient extravasation at the site of target regions such as solid tumors.

While polymer carriers used to date have the ability to attach an acceptible number of active agents, such as drugs or diagnostic agents, and possess the benefit imparted by large size, i.e., long circulation time in the blood, there is still much room for improving the targeting abilities of polymer carriers. One suggestion for improving the targeting potential of polymeric agents and thus bringing more agents to the target area, e.g., a tumor, is that targeting moieties such as monoclonal antibodies (mAb) or their fragments may be introduced to the polymer (Putnam & Kopecek, 1987). Such an "active" targeting strategy should enhance the selectivity of polymeric agent delivery system. Moreover, in the case of cancer treatment, antibody targeting has a potential to deliver anticancer drugs to smaller size tumors where the "enhanced permeability and retention (EPR)" effect is not effective. Compared to direct covalent binding of agents such as drugs to antibodies, the approach of using polymers as an intermediate agent carrier has the potential of making efficacious conjugates with high agent payload and improved aqueous solubility.

Many attempts have been made to conjugate antibodies to polymers to form drug conjugates (Putnam & Kopecek, 1995). Antibodies are often conjugated to linear polymers via their side chain functional groups through the use of activated polymer precursors (Kopecek & Duncan, 1987; Omelyanenko et al., 1996). This approach usually results in reduced receptor binding affinity (Kopecek & Duncan, 1987; Seymour et al., 1991) either due to serious changes in the chemical properties of the antibodies or due to folded configuration of polymers that imbed the targeting moiety in the randomly coiled structure. Moreover, crosslinks and aggregates of polymers could form as a result of side-chain activation.

Several approaches have been attempted to overcome the above problems. Mann et al. (1992) suggested that a polymer molecule bearing a uniquely reactive terminus for univalent attachment to proteins may avoid crosslinking antibodies and the formation of aggregates. Similarly, Kato et al. (1984) conjugated a mAb to daunomycinpoly(glutamic acid) conjugates through a single terminal thio group located at the chain end. The conjugate retained most of the antigen-binding activity of the parent antibody. Kopecek and his colleagues used polymerizable Fab' antibody fragments for better control over the size and composition of HPMA copolymers containing antibody-macromonomer units (Lu et al., 1999). Shih et al. reported site-specific attachment to the carbohydrate region of a mAb through dextran carrier (Shih et al., 1991). These studies suggest that the type of polymer as well as the way various components conjugated together are important determinants of the targeting properties of the antibody conjugated polymeric agents; however, this is still an area of ongoing study.

SUMMARY OF THE INVENTION

Technical benefits of the present invention include a polymer carrier design with sufficient or improved retention of targeted polymeric conjugates in target regions which additionally avoids one or more of the problems associated with previously available carriers or formulations.

In one embodiment, the invention includes a dendritic or "nonlinear" poly(amino acid) including a branched polymeric central initiator core. The structure of the core defines the dendritic branching characteristics of the poly(amino acid). The branched polymeric central initiator core also includes functional amine goups at the ends of branches for attachment of poly(amino acid) chains. These may include surface primary amine groups. The attached poly(amino acid) chains may take the form of inter alia, a linear structural unit, a terminal functional group at the terminus of the linear structural unit, one or more side chain structural units, and one or more functional groups at the terminus of the side chain structural units.

In one embodiment of the invention, the central initiator core may include poly(ethyleneimine) (PEI) with a molecular weight of 500–10000, and have 2 to 5000 branches. The PEI may have 2 to 250 amines suitable for initiating polymerization reactions.

In another embodiment, the central initiator core of the dendritic poly(amino acid) formed in accordance with teachings of the present invention may include an amine-containing dendrimer, such as a poly(amidoamine) (PAMAM) with a molecular weight of 359 to 116000. The poly(amidoamine) (PAMAM) may have 3 to 512 surface primary amino groups.

The dendritic poly(amino acid) may also contain a poly(lysine) central initiator core, such as branched oligo(lysine). The number of primary amines in a branched oligo(lysine) central initiator core may vary from 2 to 128.

The dendritic poly(amino acid) may have one or more terminal functional groups at the ends of the poly(amino acids) including, inter alia, an amine group, a carboxyl group, a sulfhydryl group, a vinylsulfone group, a maleimide group, or an isothiocyanatobenzyl group. The dendritic poly(amino acid) may also have one or more side-chain functional groups including inter alia, amine groups, carboxylic acid groups, hydroxyl groups, or sulfhydryl groups. Some compositions of the poly(amino acid) may be water soluble. Terminal and side-chain functional groups may affect water solubility.

The dendritic poly(amino acid) may include poly(amino acid) chains including L- and/or D-glutamic acid (Glu) repeating units, L- and/or D-aspartic acid (Asp) repeating units, L- and/or D-lysine (Lys) repeating units, cysteine (Cys) repeating units, arginine (Arg) repeating units, or histidine (His) repeating units, Ser, Tyr, or Thr (which have hydroxyl groups), Gly, Ala, Val, Leu, Ile, Thr, Trp, Phe, Tyr, or Met repeating units, or combinations thereof.

The dendritic poly(amino acid) may further include one or more targeting ligands operatively attached to one or more poly(amino acid) chains. In an exemplary embodiment, one or more targeting ligands are operatively attached to a terminal functional group. The targeting ligands may include one or more peptides, or proteins, such as annexin V, vascular endothelial growth factors (VEGF), interferon-α, tumor necrosis factor, or transferin, cyclic RGT-containing peptides, epidermal growth factor.

The targeting ligands of the dendritic poly(amino acid) may also include one or more antibodies or antibody derivatives such as single-chain antibodies, antibody fragments or monoclonal antibodies. In an exemplary embodiment, the monoclonal antibodies may be selected from anti-epithelial growth factor (EGF) receptor antibody, anti-integrin antibody, anti-VEGF receptor antibody, or anti-CD13 antibody, etc.

Targeting ligands may also include one or more peptides such as RGD-containing peptides, EGF, somatostatin, or octreotide, or small molecules or other molecules capable of binding to a cellular receptor, such as folic acid.

The dendritic poly(amino acid) may additionally include one or more therapeutic agents operatively attached to one or more poly(amino acid) chains. In an exemplary embodiment, therapeutic agents are operatively attached to one or more side-chain functional groups. Therapeutic agents in an exemplary embodiment may be chosen from a list comprising paclitaxel, docetaxel, camptothecins, epothilones, geldanamycin, etopside, doxorubicin, daunomycin, cisplatin, carboplatin, methotrexate, cyclosporin, emodin, amphotericin B, etc., or selected from the group consisting of chemotherapeutics, antibiotics, antiviral, anti-inflammatory agents, or radiosensitizers.

In another embodiment, the dendritic poly(amino acid) may include one or more diagnostic agents. The agents preferably weigh less than 1000 Da. The diagnostic agents may be operatively attached to one or more terminal or side-chain functional groups of the poly(amino acid) chains. The diagnostic agents may include organic compounds or radiopaque compounds that are suitable as CT or MRI contrast agents. The list of radiopaque compounds may include one or more radiopaque compounds containing iodine, paramagnetic and superparamagnetic metal ions. The diagnostic agents may also include paramagnetic and superparamagnetic ion chelates, radionuclides, or near-infrared fluorescent probes, such as derivatives of indocyanine green. Paramagnetic ions may include Gd, Mn, Dy, Cr, or Fe. Radionuclides may include $^{99m}$Tc, $^{111}$In, $^{97}$Ru, $^{67}$Cu, $^{64}$Cu, $^{67}$Ga, $^{68}$Ga, $^{72}$As, $8^{9}$Zr, $^{90}$Y or $^{201}$Tl.

A further embodiment of the invention is a method of synthesizing a dendritic poly(amino acid) including obtaining N-carboxyanhydride (NCA) monomers of one or more amino acids, obtaining a dendritic initiator, adding the NCA monomers and the dendritic initiator to a solvent to form a reaction mixture, and incubating the reaction mixture from 30 min to 48 hrs. The NCA monomers may be NCA monomers of glutamic acid, aspartic acid, or lysine. The dendritic initiator may include a branched polymer, oligomer or a dendrimer. More specifically, the dendritic initiator may include polyethyleneimine (PEI), poly(amidoamine) (PAMAM), or oligo(lysine).

The method of synthesizing a dendritic poly(amino acid) may include a polymerization that is carried out at a temperature range between 4° C. to 100° C., preferably at room temperature. The method of synthesis may also include deblocking of the side-chain protecting groups of the poly(amino acids), which may be carried out by bubbling hydrogen bromide (HBr) through the reaction mixture. The HBr may be bubbled through the reaction mixture for at least 30 min. The dendritic poly(amino acid) formed in the reaction may be purified by solvent extraction.

In another embodiment of the invention, there is provided a method for delivering a therapeutic or diagnostic agent to a cell, organ, or tissue in an organism, including humans by administering a composition including the dendritic poly(amino acid).

The method may further include using a pohysiological medium or carrier with the dendritic poly(amino acid). The compound including the dendritic poly(amino acid) may be introduced into the organism intravenously, intraperitoneally, intra-arterially, intratumorally, intramuscularly, intratracheally, or subcutaneously.

In another aspect of the invention, the method may include introduction of one or more diagnostic agents as part of the dendritic poly(amino acid).

A further embodiment of the invention, includes a method for improving the solubility of a compound by attaching the compound to one or more of the poly(amino acid) chains of a dendritic poly(amino acid).

The compound may be a therapeutic agent or a diagnostic agent, such as, an anti-cancer drug or a diagnostic agent for cancer.

A further embodiment of the invention involves a method for altering the pharmokinetics of a compound which includes attaching the compound to one or more poly(amino acid) chains of a dendritic poly(amino acid).

Another embodiment of the invention includes a method for enhancing the therapeutic index of a compound which may include attaching the compound to one or more poly (amino acid) chains of a dendritic poly(amino acid).

BRIEF DESCRIPTION OF THE DRAWINGS

The patent or application file contains at least on drawing executed in color. Copies of this patent or patent application publication with color drawing(s) will be provided by the Office upon request and payment the necessary fee.

The following figures form part of the present specification and are included to further demonstrate certain aspects of the present invention. The invention may be better understood by reference to one or more of these drawings in combination with the detailed description of embodiments presented herein.

DETAILED DESCRIPTION OF THE INVENTION

Figure 1:
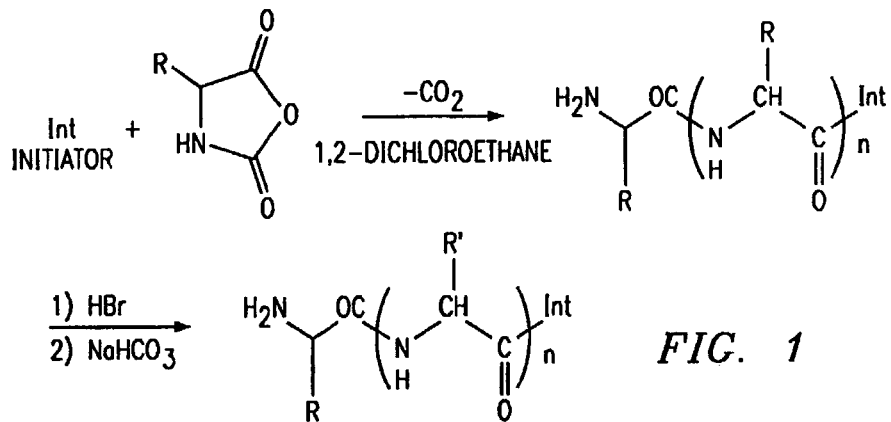
FIG. 1 illustrates a reaction scheme for synthesis of dendritic poly(amino acids) according to an embodiment of the present invention, the side chain functional group R as depicted varies depending on the amino acids used, wherein dendritic poly(L-glutamic acid) (PG) as shown, is obtained when R=CH2CH2COOCH2C6H5 and R'=CH2CH2COO—Na+, and the initiator (Int) may be PEI, PAMAM, linear poly(lysine), or branched oligo(lysine)
Figure 2A:
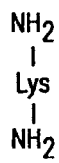
FIGS. 2A–E illustrate chemical structures of branched oligo(lysine) that may be used to initiate polymerization of dendritic poly(amino acids) according to an embodiment of the present invention.
Figure 2B:
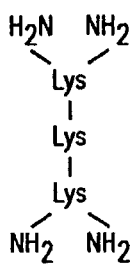
Figure 2C:
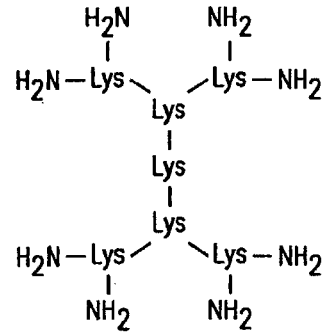
Figure 2D:
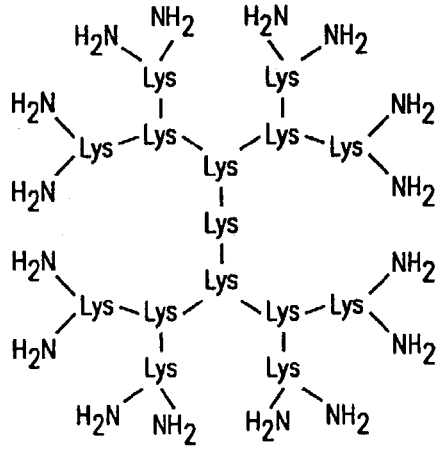
Figure 2E:
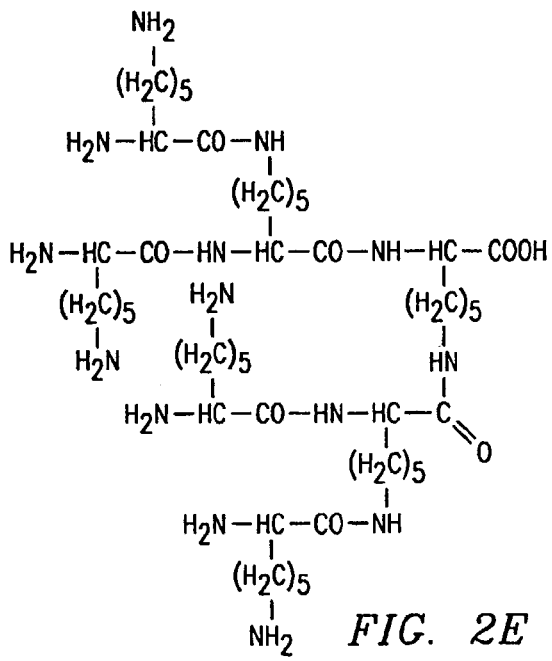

The following abbreviations are commonly used throughout the application:
CT—computer assisted tomography, a medical diagnostic test,
DCE—dichloroethane, a solvent,
DMF—dimethyl formamide, a solvent
DMSO—dimethyl sulfoxide, a solvent,
FA—folic acid, a small molecule, also a necessary nutrient,
FR—folic acid receptor, a protein found on the surface of cells to which folic acid binds,
FPLC—fast protein liquid chromatography, a chemical separation and detection technique,
GPC—gel permeation chromatography, a chemical separation and detection technique,
HBr—hydrogen bromide,
ICG—indocyanine green dye,
IXL—Ioxilan, a triiodobenzoyl derivative used as a small-molecular weight, non-ionic contrast agent,
mAb—monoclonal antibody,
MWD—molecular weight distribution,
MTT—3-(4,5-(methylthiazol-2-yl)-2,5-diphenyltetrazolium bromide, a yellow chemical cleaved only by living cells to produce a dark blue product,
NCA—N-carboxyanhydride,
—$NH_2$—amino group,
PAMAM—poly(amidoamine), a family of dendrimer molecules of various sizes with amino groups,
PAMAM-$PG_n$—PAMAM with "n" number of PG groups attached,
PBS—phosphate buffered saline, a common solvent capable of maintaining pH,
PEG—polyethylene glycol, a typically linear polymer that may be produced in a variety of lengths or molecular weights, PEI—poly(ethyleneimine), a branched polymer with amine functional groups,
PD—polydispersity,
PG—poly(L-glutamic acid), a possible poly(amino acid) chain in the present invention,
SATA—N-succinimidyl S-acetylthio acetate,
SH—sulfhydryl group,
S-PG$_n$—nonlinear PG, "n" designates the number of PG arms,
TNBS—trinitrobenzene sulfonic acid, an agent that binds to amino groups and is detectable by color,
TXL—paclitaxel, an anticancer agent,
VS—vinylsulfonyl group.

Cancer chemotherapy and many other treatments are ultimately limited by toxicity of therapeutic drugs to normal cells and tissues. In fact, many anti-cancer drugs have a detrimental effect on normal cells. There have been numerous attempts to increase the effectiveness of toxic drugs by increasing their concentration at the target site, where the drugs are needed, relative to other sites in the patient, primarily by using targeting agents. However, none of these approaches are without limitations. Thus, there remains a need to find new ways to introduce drugs into patients that result in their concentration in particular organelles, cells, tissues or organs.

Similarly, various diagnostic agents that would otherwise be useful are not suitable for routine diagnosis because of toxic side effects to non-target areas. Additionally, some diagnostic agents currently used might be more widely used or made safer to the patient if they could be properly targeted. Furthermore, all diagnostic agents for use in a particular organelle, cell, region, or tissue could benefit from increased targeting.

A polymer carrier according to the present invention may sometimes be described as "dendritic poly(amino acid)", "nonlinear polymer" "nonlinear poly(amino acid)", or "star-shaped poly(amino acid)". However, a wide variety of polymers and polymer carriers may be formed in accordance with teachings of the present invention to allow sufficient preservation of the binding affinity of the targeting units while simultaneously conjugating therapeutic or diagnostic agents to the polymers. The term "polymers" as used herein includes oligomers, co-polymers and the like. Some polymers of the invention allow high loading of the therapeutic diagnostic agents. Several characteristics of the polymer make this possible. First, the targeting agents may be attached to the surface of the polymer located away from the polymer coils, which avoids targeting moieties being embedded within the polymer coils where they are unable to access the target. Second, each macromolecule may conjugate more than one targeting unit at controlled sites to maximize the synergistic effect of multivalent interactions. The new polymer vehicle design also allows for control, during production, of the polymer's molecular weight and for control of the number of terminal functional groups and thus the number of conjugation sites (valency) for the targeting moieties. Third, the capacity to bind therapeutic or diagnostic agents is not significantly sacrificed and in many embodiments is enhanced as compared to existing targeted delivery compositions.

Dendritic poly(amino acids) of the present invention build upon the favorable properties of dendrimers. Like dendrimers, these dendritic poly(amino acid) carriers have attractive features including narrow molecular weight distribution and the presence of multiple functional groups at the polymer surface. However, unlike dendrimers, the syntheses of these carriers does not require tedious, multistep procedures, and they are very inexpensive to prepare as compared to dendrimers. Additionally, these carriers may be biodegradable and have heterofunctional groups for drug attachment and for coupling of targeting moieties.

1. Dendritic Poly(Amino Acid) Compositions

Dendritic poly(amino acids) of the present invention typically include two main components, a branched polymer central initiator core with amine groups for poly(amino acid) attachment, and one or more poly(amino acid) chains, which are directly attached to and which grow from the amine groups of the central initiator core.

The branched polyer central initiator core may include a dendritic polymer or oligomer whose primary function is to define the shape of the dendritic poly(aminoacid) and the number of poly(amino acid) chains attached to the core.

Finally, the poly(amino acid) chains contain both terminal and side-chain functional groups. The side chain functional groups provide multiple points of attachment for therapeutic agents, diagnostic agents, and/or even other polymers which are attached to and, as the term is used herein, a part of the therapeutic or diagnostic agents. These compounds may be attached to the functional groups on the poly(amino acid) chains by covalent bonds or ionic interactions. The multiple terminal functional groups on the termini of poly(amino acids) chains which may be different from the side chain functional groups, provide points of attachment for multiple targeting units such as peptides, proteins, monoclonal antibodies etc. that guide the entire construct to the target site. In certain embodiments, the terminal sites may also be used for therapeutic or diagnostic agents.

A. Central Initiator Core

In certain embodiments, the central initiator core may be any branched polymer, including dendritic polymer or branched oligomers. These molecules may contain more than two functional groups that may initiate the ring-opening polymerization of the N-carboxyanhydride of amino acids. An exemplary branched polymer is the synthetic polycation, poly(ethylenamine) (PEI). PEI possesses a high number of amine functional groups including primary, secondary, and tertiary amines. These amine groups may serve as points of operative attachment for poly(amino acid) chains. Linear or branched poly(lysine) having multiple primary amines may also be used as initiator.

Another example is branched oligomeric lysine (FIG. 2). As shown in FIG. 2, sequential propagation of Boc-Lys (Boc) may generate $2^n$ reactive NH$_2$-ends (Tam, 1988). Thus, lysine has two-reactive ends FIG. 2(A). The sequential generation of a second, third, and fourth step with Boc-Lys (Boc) will produce branched oligomeric lysine containing four (FIG. 2B), eight (FIG. 2C), and sixteen (FIG. 2D) reactive amino groups, to which the poly(amino acid) chain may be attached. A representative branched poly(lysine) having eight primary amines that could potentially be used to prepare dendritic poly(amino acids) containing eight poly(amino acid) chains is shown in FIG. 2E.

In other embodiments, the branched polymer may include a dendrimer polycation. Dendrimers are polymers with branched structures arising from concentric layers of polymerized materials with each branch ending in a functional group used for the synthesis of the succeeding generation. Each end group may react with additional monomeric units, resulting in the geometric growth of the molecular size of the polymer and the number of functional end groups. As the generations increase the morphological structure becomes spherical with functional end groups forming a shell on the surface. Dendrimer polycations and methods of preparing them are described in Tomalia et al., 1990; PCT/US83/02052; U.S. Pat. Nos. 6,113,946, 4,507,466, 4,558,120, 4,568,737, 4,587,329, 4,631,337, 4,694,064, 4,713,975, 4,737,550, 4,871,779 and 4,857,599. Dendrimer polycations generally comprise oligomeric and/or polymeric compounds attached to a core molecule. As used herein "attached" may include, but is not limited to such attachments as a covalent bond or ionic bond.

Examples of branched polymers as a central initiator core include, but are not limited to, poly(amidoamines) (PAMAM). Table 1 compares the molecular weight, size, and number of —NH$_2$-groups of two types of PAMAM dendrimers of different generations with an ammonia core or an ethylenediamine core. The typical molecular weights of PAMAM vary from 359 to 175,000 (for ammonia core) and from 517 to 233,000 (for ethylenediamine core). The number of amino functional groups typically varies from 3 to 1024. PAMAM of higher molecular weight and higher numbers of amino groups may also be used to prepare dendritic poly(amino acids).

Another example of branched polymer central initiator cores than can be used to prepare dendritic poly(amino acids) of the present invention include polypropylenimine tetraamine dendrimers available from Aldrich-Sigma Chemicals, Inc.) such as DAB-Am-4, DAB-Am-8, DAB-Am-16, DAB-Am-32, DAB-Am-64 etc that have 4, 8, 16, 32, and 64 terminal amino groups, respectively.

TABLE 1

Comparison of molecular weight, size, and number of —NH$_2$-groups of PAMAM dendrimers suitable for initiating the polymerization of nonlinear poly (amino acids)

|  | Generation | Molecular Weight | Size (nm) | No. of NH$_2$ Groups |
|---|---|---|---|---|
| Ammonia Core | 0 | 359 | 1.0 | 3 |
|  | 1 | 1044 | 1.6 | 6 |
|  | 2 | 2414 | 2.2 | 12 |
|  | 3 | 5154 | 3.1 | 24 |
|  | 4 | 10630 | 4.0 | 48 |
|  | 5 | 21590 | 5.4 | 96 |
|  | 6 | 43510 | 6.8 | 192 |
|  | 7 | 87340 | 8.4 | 384 |
| Ethylenediamine Core | 0 | 517 | 1.4 | 4 |
|  | 1 | 1430 | 1.9 | 8 |
|  | 2 | 3256 | 2.6 | 16 |
|  | 3 | 6909 | 3.6 | 32 |
|  | 4 | 14000 | 4.4 | 64 |
|  | 5 | 29000 | 5.7 | 128 |
|  | 6 | 58000 | 7.2 | 256 |
|  | 7 | 116000 | 8.8 | 512 |

The above PAMAM dendrimers are derived from an ammonia core and an ethylenediamine core, respectively.

B. Poly(Amino Acid) Chains

Poly(amino acids) are ideal for use as a carrier polymer for a variety of reasons, including the following factors:

1) Given the choice of poly(amino acids) to obtain various side-chain functional groups, multiple drug/contrast agent molecules may be attached to each polymer chain, potentially resulting in an overall amplification of associated drug effects, contrast effects or efficiencies in administration.

2) The use of neutral or negatively charged polymers may lead to reduced nonspecific interaction and reduced uptake in normal organs.

3) The linear counterpart of dendritic PG has been used experimentally and clinically as a drug carrier for anticancer agents due to its water solubility, high payload, nontoxicity, and nonimmunogenicity (Li C, Yu D-F, Newman R A, Cabral F, Wallace S. Complete regression of well-established tumors using a novel water-soluble poly(L-glutamic acid)-paclitaxel conjugate. Cancer Res. 58: 2404–2409, 1998.; Li C, Price J E, Milas L, Hunter N R, Ke S, Yu D-F, Charnsangavej C, Wallace S. Antitumor activity of poly(L-glutamic acid)-paclitaxel on syngeneic and xenografted tumors. Clin. Cancer Res. 5: 891–897, 1999; Todd R, Sludden J, Boddy A V, Griffin M J, Robson L, Cassidy J, Bissett D, Main M, Brannan M D, Elliott S, Fishwick K, Verrill M, Calvert H. Phase I and pharmacological study of CT-2103, a poly(L-glutamic acid)-paclitaxel conjugate. Amer Assoc Clin Oncol Proceedings [Abs. #439], 2001.).

4) Terminal functional groups may serve as points of attachment for targeting or homing ligands. It is possible to significantly enhance binding affinity through a multivalency cluster effect by conjugating multiple target-homing ligands to dendritic polymeric carriers.

5) In certain embodiments, poly(amino acid) chains attached to the central initiator core may include monomers of glycine, alanine, valine, leucine, isoleucine, methionine, proline, phenylalanine, trytophan, asparagine, glutamine, serine, threonine, aspartic acid, glutamic acid, tryosine, cysteine, lysine, arginine, histidine, or combination thereof.

6) In certain embodiments, the number of monomers in an individual poly(amino acid) chain may be about 3, about 10, about 25, about 50, about 75, about 100, about 200, about 300, about 400, about 500, about 600, about 700, about 800, about 900, about 1000, and any integer derivable therein and any range derivable therein. Of course, in various aspects, mixtures of poly(amino acid) chains of different lengths may be used. In other embodiments, the number of side-chain functional groups on a particular poly(amino acid) chain may be about 3, about 10, about 25, about 50, about 75, about 100, about 200, about 300, about 400, about 500, about 600, about 700, about 800, about 900, about 1000, and any integer derivable therein and any range derivable therein.

C. Terminal Functional Groups

The terminal functional groups on the surface of some nonlinear poly(amino acids) may be primary amines (—NH$_2$). They may be coupled to homing ligands through a variety of —NH$_2$ reactive groups. Alternatively, —NH$_2$ may be further converted to other functional groups such as sulfhydryl (—SH), carboxyl (—COOH), maleiimide, vinyl sulfone., aldehyde (—CHO), isothiocyanatobenzyl group (—SCN) etc. with or without the use of spacers.

2. Synthesis of Dendritic Poly(Amino Acids)

A. General Description

The invention includes ring-opening polymerization of N-carboxyanhydrides of amino acids (NCAs) as known in the art using amine-containing dendrimers or branched polymers as initiators. In one embodiment, the dendritic poly(amino acids) may be synthesized according to the following method. First, the side chain protected amino acid (if the amino acid has a side-chain functional group) or amino acid is converted to the corresponding N-carboxyanhydride. This conversion may be done according to Goodman with some modifications (Fuller et al., 1975). Specifically, in place of the hazardous phosgene gas used in Goodman, the more convenient solid triphosgene may be used. The NCA is then polymerized in a solvent such as 1,2-dichloroethane (DCE) using an initiator such as PEI or PAMAM as the initiator core. It is often advisable that the reaction mixture be allowed to stand for sufficient time such that a favorable yield results. The reaction mixture may then be deblocked. This may be done, for example, in the case of benzyl protecting groups in dendritic poly(γ-benzyl glutamic acid) or in the case of N-carbobenzoxy (Cbz) protecting group in poly(Nε-Cbz-Lysine) by bubbling HBr gas into the solution. Finally, the dendritic poly(amino acid) product may be recovered by precipitatation with ether or methanol.

B. Controlling Molecular Weight and Density of Surface Amino Groups

The molecular weight of dendritic poly(amino acids) may be controlled by varying the ratio between the number of N-carboxyanhydrides of amino acid monomers and the number of initiator cores. Increasing this ratio increases the molecular weight of the dendritic poly(amino acids). The density of surface amino groups on the dendritic poly(amino acids) may also be controlled by selecting initiator cores of different molecular weights. As the molecular weight of an initiator core increases a corresponding increase occurs in a number of surface amino groups, in concurrence with an increase in the number of branching poly(amino acid) chains.

3. Compositions Including Drugs, Other Therapeutic Agents, and/or Diagnostic Agents In certain embodiments, drugs, other therapeutic agents such as DNA, and/or diagnostic agents may be physically or chemically attached to poly(amino acid) chains of a dendritic poly(amino acids) of the present invention. The poly (amino acid) chains not only serve as flexible linkers to control spacing of ligands, but they may also carry multiple functional groups allowing operative attachment of multiple agents. There are several advantages to using dendritic poly(amino acids) of the present invention to deliver drugs, other therapeutic agents, and/or diagnostic agents. One advantage is that high payloads of water-insoluble or slightly water-soluble agents may be conjugated to selected carriers to achieve high aqueous solubility. This is possible because certain dendritic poly(amino acid) carriers are often water soluble and associated poly(amino acid) chains generally contain many locations to which water-insoluble or slightly water-soluble agents may bind. The dendritic poly (amino acids) are typically water soluble if their side chains contain water-soluble functional groups such as carboxyl, amino, or hydroxyl groups. A second advantage is that operatively attached agents may be efficiently transported to targeted organelles, cells, tissues, organs or organisms if targeting ligands are also operatively attached to the carriers of the present invention. The term "operatively attached" is used herein to refer to any physical or chemical attachment such as but not limited to covalent or ionic bonding, london dispersion forces, or van der Waals forces.

A. Compositions Including Drugs

A variety of drugs may be operatively attached to the dendritic poly(amino acids) of the present invention. Non-limiting examples of common drugs that may be operatively attached include chemotherapeutics, antibiotics, antivirals, radionuclides, immunotherapeutics, genetic constructs, anti-inflammatories and radiosensitizers. The types of additional drugs that may be operatively attached to the poly(amino acid) chains will be readily apparent to one of skill in the art from the disclosures herein and are thus encompassed by the present invention.

i. Chemotherapeutic Agents

The term "chemotherapy" refers to the use of drugs to treat cancer. A "chemotherapeutic agent" is used to connote a compound or composition that is administered in the treatment of cancer. One subtype of chemotherapy known as biochemotherapy involves the combination of a chemotherapy with a biological therapy.

Chemotherapeutic agents include, but are not limited to:
5-fluorouracil,
6-hydroxy-2-(4-hydroxyphenyl)-3-[4-(2-piperidinoethoxy)benzol[b]thiopene,
actinomycin D, adrenocorticosteroids, adrenalcortical suppressant, amsacrine, aminoglutethimide, anthracenediones,
bleomycin, busulfan,
camptothecin, carboplatin, caproate, chlorambucil, cisplatin (CDDP), carboplatin, carmustine, cyclophosphamide, cytarabine,
dacarbazine, dactinomycin, daunorubicin, dexamethasone, diethylstilbestrol, doxorubicin,
epirubicin, epothilones, estrogen receptor binding agents, ethinyl estradiol, etoposide (VP16),
farnesyl-protein transferase inhibitors, floxuridine, fludarabine, fluoxymesterone, flutamide,
geldanamycin, gemcitabine,
hexamethylmelamine, hydroxyprogesterone, hydroxyurea,
idarubicin, ifosfamide, irinotecan (CPT-11),
L-asparaginase, leuprolide, lomustine,
mechlorethamine, medroxyprogesterone acetate, megestrol acetate, melphalan, mercaptopurine, methotrexate, methyl hydrazine derivatives, mithramycin, mitomycin, mitotane, mitoxantrone,
navelbine, nitrosurea,
pentostatin, platinum coordination complexes, plicamycin, prednisone, procarbazine,
raloxifene,
semustine, streptozocin, substituted urea,
tamoxifen, taxol (paclitaxel), taxotere (docetaxel), teniposide, testosterone propionate, thioguanine, thiotepa, temazolomide (an aqueous form of DTIC), transplatinum, tretinoin, topotecan,
vinblastine, vincristine, vinorelbine,
or any analog or derivative variant of the foregoing.

These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into one or more of the following categories:
alkyl sulfonates, alkylating agents, antimetabolites, antitumor antibiotics,
biological response modifiers,
corticosteroid hormones,
epipodophyllotoxins, ethylamines,
folic acid analogs,
hormone agents and antagonists,
methylmelamines, mitotic inhibitors,
natural products, nitrogen mustards, nitrosoureas,
purine analogs, pyrimidine analogs,
taxoids, triazines,
vinca alkaloids,
and any analog or derivative variant thereof.

Chemotherapeutic agents and methods of administration, dosages, etc. are well known to those of skill in the art (see for example, the "Physicians Desk Reference", Goodman & Gilman's "The Pharmacological Basis of Therapeutics" and in "Remington's Pharmaceutical Sciences" and may be combined with the invention in light of the disclosures herein. Some variation in dosage will necessarily occur depending on the condition of the subject being treated. The person responsible for administration will, in any event, determine the appropriate dose for the individual subject. The present invention, because of its targeting ability, may allow the administration of lower doses than would be normally administered while maintaining suitable efficacy. Alternatively, because drug delivery may be targeted, higher doses than normal may be used because toxicity to other cells, tissues and organs may be reduced.

ii. Radiotherapeutic Agents

Radiotherapeutic agents include radiation and waves that induce DNA damage for example, γ-irradiation, X-rays, proton beam irradiation, UV-irradiation, microwaves, electronic emissions, radioisotopes, and the like. Therapy may be achieved by irradiating the localized tumor site with the above forms of radiation.

Radiotherapeutic agents and methods of administration, dosages, etc. are well known to those of skill in the art, and may be combined with the invention in light of the disclosures herein. For example, dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the halflife of the isotope, the strength and type of radiation emitted, and the uptake by the neoplastic cells.

The present invention may be used to deliver radiotherapeutic agents in the body to a specific cell, tissue, or organ.

Additionally, it may be used to deliver chemotherapeutic or other agents in combination with radiotherapy. Such agents may provide a synergystic effect with radiotherapy or may be activated by radiotherapy.

iii. Immunotherapeutic Agents

Immune Stimulators.

A specific type of immunotherapy uses an immune stimulating molecule as an agent, or in conjunction with another agent, for example, cytokines such as: Interleukin (IL)-2, IL-4, IL-12, or granulocyte macrophage conony stimulating factor (GM-CSF), tumor necrosis factor (TNF); interferons α, β, and γ; F42K and other cytokine analogs; a chemokine such as: macrophage inflammatory protein (MIP)-1, MIP-1beta, macrophage chemoattractant protein (MCP)-1, RANTES, IL-8; or a growth factor such as FLT3 ligand. All of these agents may be delivered in a targeted fashion using the present invention. Because inappropriate delivery of immune stimulating molecules may have very negative side-effects, such as autoimmune disesase, the targeting capacity of the present invention may prove especially useful in immune stimulant therapy.

One particular cytokine contemplated for use in the present invention is tumor necrosis factor. Tumor necrosis factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF may be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α, also has been found to possess anti-cancer activity.

Another cytokine specifically contemplated for use in the present invention is interferon alpha. Interferon alpha has been used in the treatment of hairy cell leukemia, Kaposi's sarcoma, melanoma, carcinoid, renal cell cancer, ovary cancer, bladder cancer, non-Hodgkin's lymphomas, mycosis fungoides, multiple myeloma, and chronic granulocytic leukemia.

iv Oher Biological Agents

It is contemplated that other agents may be used in combination with the present invention to improve the therapeutic efficacy of treatment. These additional agents include: agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents.

It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases in intercellular signaling by elevating the number of GAP junctions would increase the anti-hyperproliferative effects on the neighboring hyperproliferative cell population.

In other embodiments, cytostatic or differentiation agents may be used in combination with the present invention to improve the anti-hyperproliferative efficacy of the treatments.

Inhibitors of cell adhesion are contemplated to improve the efficacy of the present invention. Examples of cell adhesion inhibitors are focal adhesion kinase (FAKs) inhibitors and lovastatin. It is further contemplated that other agents that increase the sensitivity of a hyperproliferative cell to apoptosis, such as, for example, the antibody C225, could be used in combination with the present invention to improve the treatment efficacy.

Although the above discussion focuses on anti-cancer agents, it will be apparent to one skilled in the art that after pharmaceuticals or therapeutic agents may be targeted to a specific cell, tissue, organ or organism using the dendritic poly(amino acid) of the present invention.

B. Compositions Including Other Therapeutic Agents

In addition to drugs, other types of therapeutic agents may also be operatively attached to the dendritic poly(amino acid) carriers of the present invention. One important, yet non-limiting, example of a therapeutic agent that may be functionally attached to the carrier of the present invention is a nucleic acid for purposes of gene therapy. In fact, when positively charged functional groups are introduced into the side-chains of each poly(amino acid) chain, the polymers may form complexes with negatively charged DNA and be used as non-viral delivery vehicles for the delivery of therapeutic nucleic acids.

Gene therapy now is becoming a viable alternative to various conventional therapies, especially in the area of cancer treatment. Limitations such as long term expression of transgenes and immuno-destruction of target cells through the expression of vector products, which have been said to limit the implementation of genetic therapies, are not concerns in cancer therapies, where destruction of cancer cells is desired.

A tumor cell's resistance to agents, such as chemotherapeutic and radiotherapeutic agents, represents a major problem in clinical oncology. It is important in gene transfer therapies, especially those involving treatment of cancer, to kill as many of the cells as quickly as possible. One goal of current cancer research is to find ways to improve the efficacy of one or more anti-cancer agents by combining such an agent with gene therapy. Thus, the use of "combination" therapies may be favored. Such combinations may include gene therapy and radiotherapy or chemotherapy. For example, Roth et al. (1996) have demonstrated that a combination of DNA damaging agents and p53 gene therapy provides increased killing of tumor cells in vivo. In another example, the herpes simplex-thymidine kinase (HS-tK) gene, when delivered to brain tumors by a retroviral vector system, successfully induced susceptibility to the antiviral agent ganciclovir (Culver et al., 1992).

Yet another type of combination therapy involves the use of multi-gene therapy. In this situation, more than one therapeutic nucleic acid may be transferred into a target cell. The nucleic acids may encode proteins from the same functional group (e.g., both tumor suppressors, both cytokines, etc.) or from different functional groups (e.g., a tumor suppressor and a cytokine). By presenting particular combinations of therapeutic nucleic acids to a target cell, it may be possible to augment the overall effect of either or both expressed proteins on the physiology of the target cell.

It may also be possible to administer nucleic acids that exert effects without being expressed as proteins, for instance, through RNA blocking or induction of DNA silencing.

In the context of the present invention, it is contemplated that the dendritic poly(amino acid) carrier of the current invention could be used for gene therapy, including multi-gene therapy. Such gene therapy is expected to alter the transcription of cellular genes, alter RNA processing, increase expression of the encoded protein or proteins, thereby altering the phenotype of the cell. The carrier of the present invention could be used to efficiently deliver nucleic acids to target sites, such as cancer cells.

C. Diagnostic Agents

The invention also relates to an in vivo imaging method wherein diagnostic agents are delivered to target regions of a subject for imaging a target area, such as an area exhibiting a disease state. In specific embodiments, the disease state may be a cancerous tumor or tumor cells. This method involves administering to a subject an imaging-effective amount of a diagnostic agent operatively attached to a dendritic poly(amino acid) carrier and detecting the binding of the diagnostic agent to the target area, e.g. a tissue. The term "in vivo imaging" refers to any method which permits the detection of a diagnostic agent delivered with the dendritic poly(amino acid) of the present invention that specifically binds to a target area located in the subject's body. A "subject" may be a mammal, including a human. An "imaging effective amount" means that the amount of the detectable-labeled agent, such as a monoclonal antibody, or fragment thereof, administered is sufficient to enable detection of the agent to the target area.

One of the advantages of delivering a diagnostic agent using the dendritic poly(amino acid) carriers of the present invention is that the diagnostic agent is gradually excreted when delivered in this manner. Therefore the delivery of diagnostic agents using the dendritic poly(amino acid) carriers of the present invention may find applications where improved diagnostic procedures involving blood pool imaging, such as local tissue perfusion or vascular imaging, are required. The gradual excretion of the contrast agent may also be beneficial in that it may facilitate optimal imaging and reduced toxicity. Thus, the water-soluble carriers of the present invention might be successfully applied to the design of diagnostic carriers for radiopaque contrast agents such as ionic or nonionic iodinated compounds for computed tomographic imaging. They may be applied to the design of carriers for paramagnetic as well as superparamagnetic metal ions agent such as gadolinium and iron for magnetic resonance imaging. They may also be applied to the design of carriers for near-infrared fluorescent contrast agent such as indocyanine green for optical imaging.

The diagnostic agent may be any biocompatible or pharmacologically acceptable agent which may be operatively attached to the dendritic poly(amino acid) of the present invention. In a non-limiting example, the biocompatible or pharmacologically acceptable agent is an imaging agent including the commercially available agents for use in computer assisted tomography (CT), magnetic resonance imaging (MRI), fluoroscopy, near-infrared optical imaging, positron emission tomography, single photon emission computerized tomography, and x-ray. Examples of these agents include iodinated compounds for CT, paramagnetic an superparamagnetic metal ions such as Gd, Mn, Dy, Cr, and Fe for MRI, near-infrared fluorescent probes such as derivatives of indocyanine green for near-infrared optical imaging, and radionuclides such as $^{99m}$Tc, $^{111}$In, $^{97}$Ru, $^{67}$Cu, $^{64}$Cu, $^{67}$Ga, $^{68}$Ga, $^{72}$As, $^{90}$Y, $^{89}$Zr, and $^{201}$Tl for nuclear imaging. Radionuclide or paramagnetic agents may be bound to a dendritic poly(amino acid) carrier with or without spacers and by using chelators. Chelators which are often used to bind metal ions include but are not limited to diethylenetriaminepentaacetic acid (DTPA), p-aminobenzyl-diethylenetriaminepentaacetic acid (p-NH$_2$-Bz-DTPA), ethylene diaminetetracetic acid (EDTA), 1,4,7,10-tetraazacyclododecane-N,N',N'',N'''-tetraacetic acid. (DOTA), 2-p-aminobenzyl-1,4,7,10-tetraazacyclododecane-N,N',N'',N'''-tetraacetic acid (p-NH$_2$-Bz-DOTA), 1,4,7,10-tetraazacyclododecane-1, 4,7,10-tetrakis(methylene phosphonic acid) (DOPA), and 3,6,9,15-tetraazabicyclo[9.3.1]pentadeca-1(15),11,13-triene-3,6,9-triacetic acid (PCTA), etc.

The types of additional diagnostic agents that may be operatively attached to the poly(amino acid) chains will be readily apparent to one of skill in the art from the disclosures herein and are thus encompassed by the present invention.

4. Targeting Ligands.

In certain embodiments, at least one targeting ligand directed to an organelle, cell, tissue, or organ is operatively attached to the poly(amino acid) chains of the dendritic poly(amino acid) carrier of the present invention. In certain embodiments, these targeting ligands are conjugated to the terminal functional groups present on the poly(amino acid) chains. This location preserves the effectiveness of the targeting agents by keeping them away from the polymer coils and by preventing polymer cross-linking. The terminal functional groups (—NH$_2$, —COOH, —SH, vinyl sulfonyl etc. are different from the core functional groups of the dendritic poly(amino acids) and may thus be site-selectively modified to conjugate multiple targeting units without affecting drug, other therapeutic agent, or diagnostic agent attachment. It is contemplated that any targeting agent described herein or known to one of ordinary skill in the art may be used in the compositions and methods of the present invention, either alone or in combination with other targeting agents.

Various agents for targeting molecules to specific cells, tissue, organs and organisms are known to those of ordinary skill in the art and may be used in the methods and compositions of the present invention. In certain non-limiting examples, a targeting agent may comprise a protein, such as a receptor protein (for example complimentarily determinant (CD)$_4$, CD8, annexin V or soluble fragments thereof); an antibody, an antibody fragment; a peptide;

cytokine; a growth factor hormone; lymphokine; a nucleic acid which binds corresponding nucleic acids through base pair complementarity, or a combination thereof (U.S. Pat. No. 6,071,533). In other embodiments targeting agents may include EGF, VEGF, transferrin, an anti-prostate specific membrane antigen antibody, endothelial specific peptides and bone specific ligands. In still other embodiments, the targeting ligand may comprise a cellular receptor-targeting ligand, a fusogenic ligand, a nucleus targeting ligand, or a combination thereof (U.S. Pat. No. 5,908,777), or an integrin receptor ligand, described in U.S. Pat. No. 6,083,741. Other small molecules or molecules which bind to a cell surface molecule, for example, folic acid, may also be used.

One method for introducing targeting ligands onto the termini of the poly(amino acid) chains of the dendritic poly(amino acid) carriers of the present invention is to employ sulfydryl groups. Many targeting ligands such as proteins, antibodies, antibody fragments, peptides, and single chain antibodies (ScFv), may be designed to have sulfhydrl groups (SH) introduced at specific sites. SH groups may, therefore, be operatively attached by any one of the methods well known in the art at locations on the ligands which are to be attached to the poly(amino acid) chains. SH-reactive agents, such as vinyl sulfonyl groups or maleimide, may also be operatively attached by any one of the methods well known in the art to the termini of the poly(amino acid) chains which are to be attached to the targeting ligands with or without a bifuntional agent spacer. In one non-limiting example the bifunctional agent may be a polymer such as poly(ethylene glycol) (PEG). In other non-limiting examples, the bifunctional agent may be succinimidyl maleimido-PEG (NHS-PEG-Maleimide), succinimidyl-4-(N-maleimidomethyl)-cyclohexane-1-carboxylate (SMCC), N-succinimidyl(2'-pyridyldithio)propionate (SPDP), etc., which may be used to introduce functionalized end groups that interact with SH-containing groups through a disulfite bridge or sulfoether linkages. The targeting ligands, with SH groups operatively attached, are then reacted with the dendritic poly(amino acids), with SH-reactive group operatively attached to their poly(amino acid) chains, such that the targeting ligands become operatively attached to the poly(amino acid) chains of the dendritic poly(amino acids).

5. Compositions Including Other Polymers

In addition to drugs, other therapeutic agents, and diagnostic agents, and other polymers such as polyethylene glycol may also be operatively attached to the poly(amino acid) chains of the dendritic poly(amino acid) carrier of the present invention. Like targeting ligands, other polymers may be used to modify the biodistribution properties of the dendritic poly(amino acid) carrier. These polymers may be operatively attached to either the side-chain functional groups or the terminal functional groups of the poly(amino acid) chains.

6. Cancer Treatment

It is contemplated that the present invention may find particular use in the treatment of cancer. A drug or other therapeutic agent (discussed before) may be delivered to a cell, tissue or organism for the treatment of cancer using the dendritic poly(amino acid) carrier of the present invention. One or more agents effective in the treatment of hyperproliferative disease, such as, for example, an anti-cancer agent may be used. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the life-span of a subject with a cancer. Anti-cancer agents include, for example, chemotherapy agents (chemotherapy), radiotherapy agents (radiotherapy), immune therapy agents (immunotherapy), genetic therapy agents (gene therapy), hormonal therapy, other biological agents (biotherapy) and/or alternative therapies. Such an agent may be provided either alone or in a combined amount with another agent in an amount effective to kill or inhibit proliferation of a cancer cell.

It is contemplated that cancers that may be treated by the current invention include, but are not limited to cancer of the lung, upper airway primary or secondary, head or neck, bladder, kidneys, pancreas, mouth, throat, pharynx, larynx, esophagus, brain, liver, spleen, kidney, lymph node, small intestine, pancreas, blood cells, colon, stomach, breast, endometrium, prostate, testicle, ovary, skin, bone marrow and blood cancer. Administration of the anti-cancer agent or agents to a cell, tissue or organism may follow general protocols for the administration of chemotherapeutics, taking into account the toxicity, if any. It is expected that the treatment cycles would be repeated as necessary. In particular embodiments, it is contemplated that various additional agents may be administered in any combination with the present invention.

7. Pharmaceutical Preparations

Pharmaceutical compositions of the present invention include an effective amount of one or more dendritic poly(amino acids), drugs, other therapeutic agents, diagnostic agents, polymer, and/or additional agents dissolved or dispersed in a pharmaceutically acceptable medium. The phrases "pharmaceutical or pharmacologically acceptable" refers to molecular entities and compositions that do not usually produce an adverse, allergic or other untoward reaction when appropriately administered to an animal, such as a human. The preparation of a pharmaceutical composition will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards. The dosage, formulation and delivery may be selected for a particular therapeutic application such as those described by Gonda (1990).

As used herein, "pharmaceutically acceptable medium" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289–1329). Except insofar as any conventional carrier is incompatible with the active ingredient, its use in the therapeutic or pharmaceutical compositions is contemplated.

The actual dosage amount of a composition of the present invention administered to an animal or patient may be determined by physical and physiological factors such as body weight, severity of condition, the type of disease being treated, previous or concurrent therapeutic interventions, idiopathy of the patient and by the route of administration. The practitioner responsible for administration will, in any event, determine the concentration of active ingredient(s) in a composition and appropriate dose(s) for the individual subject.

In certain embodiments, pharmaceutically acceptable compositions may comprise, for example, at least about 0.1% of an active compound. In other embodiments, the active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 75 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., may be administered, based on the numbers described above. Due to efficiencies of the present invention, the dosages of active compound may be less than the amounts currently administered. Alternatively, greater doses of compounds than are currently administered may be rendered safer by the present invention and thus used in patients.

The composition may comprise various antioxidants to retard oxidation of one or more component. Additionally, the prevention of the action of microorganisms may be brought about by preservatives such as various antibacterial and antifungal agents, including but not limited to parabens (e.g., methylparabens, propylparabens), chlorobutanol, phenol, sorbic acid, thimerosal or combinations thereof.

The pharmaceutically acceptable composition or component of such a composition or additional agent may be formulated in buffered solution at a range of different pH values so that the composition may exist in neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups may also be derived from inorganic bases such as for example, sodium, potassium, ammonium, calcium or ferric hydroxides; or such organic bases as isopropylamine, trimethylamine, histidine or procaine.

The composition must be stable under the conditions of manufacture, storage and delivery and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition may be brought about by the use in the compositions of agents delaying absorption, such as, for example, aluminum monostearate, gelatin or combinations thereof.

8. Kits

Any of the compositions described herein may be provided in a kit. In a non-limiting example, a dendritic poly(amino acid) of the present invention a drug, another therapeutic agent, a diagnostic agent, a targeting ligand, and an additional agent covalently coupled to and/or physically trapped in the polymer may be provided in a kit. The kit may also contain means for delivering the formulation such as, for example, a syringe for systemic administration, an inhaler or other pressurized aerosol canister.

The kits may include a suitably aliquoted dendritic poly (amino acid) of the present invention composed of, a drug, another therapeutic agent, a diagnostic agent, a targeting ligand and/or additional agent compositions of the present invention, chemically coupled to and/or physically trapped in the polymeric carrier. The therapeutic components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also may contain a second, third or other additional container into which the additional components may be separately placed. However, various combinations of components may be placed in a single vial. The kits of the present invention also will typically include a means for containing the aerosol formulation, one or more components of an aerosol formulation, additional agents, and any other reagent containers in close confinement for commercial sale. Such containers may include injection or blow-molded plastic containers into which the desired vials are retained. The kit may have a single container, or it may have distinct container for each compound.

When the components of the kit are provided in one or more liquid solutions, the liquid solution is an aqueous solution, with a sterile aqueous solution being particularly preferred. However, the components of the kit may be provided as dried powder(s). When reagents and components are provided as a dry powder, the powder may be reconstituted by the addition of a suitable solvent. It is envisioned that the solvent may also be provided in another container means.

The container means will generally include at least one vial, test tube, flask, bottle, syringe and/or other container means, into which a pharmaceutically acceptable formulation of the pharmaceutically composition, a component of an aerosol formulation and/or an additional agent formulation are suitably allocated. The kits may also include a second container means for containing a sterile, pharmaceutically acceptable buffer and/or other diluent.

The kits of the present invention may include a means for containing the vials in close confinement for commercial sale, such as, e.g., injection or blow-molded plastic containers into which the desired vials are retained.

Irrespective of the number or type of containers, the kits of the invention may also include, or be packaged with, an instrument for assisting with the delivery of the aerosol formulation within the body of an animal. Such an instrument may be a syringe, an inhaler, air compressor or any such medically approved delivery vehicle.

The following examples are included to demonstrate preferred embodiments of the invention. It should be appreciated by those of skill in the art that the techniques disclosed in the examples which follow represent techniques discovered by the inventors to function well in the practice of the invention, and thus may be considered to constitute preferred modes for its practice. However, those of skill in the art should, in light of the present disclosure, appreciate that may changes may be made in the specific embodiments which are disclosed and still obtain a like or similar result without departing from the spirit and scope of the invention.

EXAMPLES

Example 1

Synthesis of a Dendritic Poly(Amino Acid) Employing L-glutamic Acid

In non-limiting examples, dendritic poly(amino acids) with L-glutamic acid repeating units were synthesized using poly(amidoamine) dendrimer (PAMAM) as an initiator core and, separately, using poly(ethylenimine) (PEI) as the initiator core. The use of PAMAM as an initiator produced a nonlinear dendritic poly(amino acid), the use of branched PEI as an initiator produced a branched dendritic poly (amino acid). Other initiator core that may be used include linear poly(lysine) and branched oligo(lysine) (for structure, see FIG. 2). The use of linear poly(lysine) an an initiator core would produce comb-like dendritic poly(amino acids), and the use of branched oligo(lysine) would produce branched dendritic polyamino acid).

The reaction scheme for the preparation of dendritic PG polymers is presented in FIG. 1. Four compositions of PAMAM-PG$_n$ (where "n" indicates the number of terminal —NH$_2$ groups and thus the number of PG arms) and two compositions of PEI-PG were synthesized. PAMAM-PG$_8$ was obtained from first-generation PAMAM with 8 surface NH$_2$ and PAMAM-PG$_{16}$ was obtained from second-generation PAMAM with 16 surface NH$_2$ groups. The results are summarized in Table 2.

TABLE 2

Synthesis of branched and nonlinear glutamic acid polymers

| Polymer | Ratio | Mn (calc) | Mn (GPC) | Yield (%) | Number of NH$_2$ per Polymer |
|---|---|---|---|---|---|
| PAMAM-PG$_8$ | | | | | |
| Run 1 | 60 | 61186 | 46160 | 33.5 | 20.6 |
| Run 2 | 30 | 30593 | 18750 | 79.8 | 9.8 |
| Run 3 | 15 | 15297 | 11020 | 87.0 | 6.3 |
| PAMAM-PG$_{16}$ | 30 | 65176 | 89960 | 82.8 | 43.6 |
| PEI-PG | | | | | |
| Run 1 | 80 | 144000 | 127270 | 80.1 | 39.7 |
| Run 2 | 20 | 36745 | 26820 | 88.6 | 9.6 |

Polymerization of the carboxyanhydride of L-glutamic acid (Glu-NCA) in all the runs progressed homogeneously in DCE or mixed solvent of DMSO and DCE. All samples except that from Run 1 were obtained in high yields over 80%. Before using PAMAM it is necessary to evaporate the methanol it is solvated in and dry the material under vacuum. In Run 1, the co-solvent DMSO was not removed prior to treatment with HBr. DMSO appeared to interfere with the deesterification process, resulting in a lower yield.

The number of primary amino groups per polymer chain was determined by a calorimetric TNBS assay (Table 2). PAMAM-PG$_8$ with molecular weight of 15K–30K had 6–10 amino groups per polymer. These numbers agreed well with the expected 8 amino groups. PEI-PG with the molecular weight of 36 K had ~10 terminal amino groups. This result suggest that in addition to primary amines, secondary and tertiary amines may also be involved in PEI initiated polymerization of Glu-NCA. It is noted that when the molecular weights reached >60K, the number of primary amino groups per polymer chain for both PAMAM-PG$_n$ and PEI-PG were much higher than expected (Table 2). This may be due to errors introduced while calculating [NH$_2$] of higher molecular weight polymers using lower molecular weight polymers as references. Nevertheless, the data confirmed that all polymers have multiple primary amino groups terminated at PG chains. As expected, the number of measured amines in PAMAM-PG16 polymer was approximately 2-fold that of PAMAM-PG$_8$ of similar molecular weight (43.6 vs. 20.6, Table 2). Our data demonstrate that the molecular weight of branched PG polymers may be simply controlled by varying the molar ratio between NCA monomers and PEI or PAMAM, and that the density of surface amino groups may be precisely controlled by using PAMAM or PEI of different molecular weights (Table 2).

Poly(L-glutamic acids) are highly charged in solution. Accurate characterization of their molecular weight, molecular weight distribution (MWD), and hydrodynamic properties in aqueous solution is essential for understanding the in vivo fate and targetability of these types of polymers. A gel permeation chromatography (GPC) system with a combined differential viscometer, light scattering, and refractometer (Viscoteck, Houston, Tex.) was used to characterize the intrinsic viscosity, MWD, Mark-Houwink constants, and branching information of various PG polymers synthesized. These data are summarized in Table 3.

TABLE 3

Molecular weight and hydrodynamic properties of branched glutamic acid polymers

| Polymer | Mw | Mn | Mw/Mn | Intrin. Vis. (dL/g) | Hydrodynamic Radius (nm) | Mark-Houwink Values a | K × 10$^3$ |
|---|---|---|---|---|---|---|---|
| PAMAM-PG$_8$ | | | | | | | |
| Run 1 | 56120 | 46160 | 1.22 | 0.342 | 6.84 | 0.658 | 0.29 |
| Run 2 | 32250 | 18750 | 1.72 | 0.191 | 4.91 | 0.755 | 0.11 |
| Run 3 | 15540 | 11020 | 1.41 | 0.128 | 3.30 | 0.783 | 0.085 |
| PAMAM-PG$_{16}$ | 96460 | 89960 | 1.07 | 0.342 | 8.09 | 0.267 | 2.940 |
| PEI-PG | | | | | | | |
| Run 1 | 149970 | 127270 | 1.18 | 0.733 | 12.1 | 0.549 | 1.13 |
| Run 2 | 44860 | 26820 | 1.67 | 0.275 | 6.14 | 0.719 | 0.17 |
| Linear PG | | | | | | | |
| 13K | 7868 | 4697 | 1.68 | 0.06 | 2.21 | 0.90 | 0.03 |
| 13K | 24390 | 20440 | 1.19 | 0.215 | 4.61 | 1.125 | 0.041 |
| 49K | 45690 | 36200 | 1.26 | 0.321 | 6.18 | 0.901 | 0.025 |

Polydispersity (PD) is the ratio of the mass-averaged molecular weight (Mw) of a polymer to its number-averaged molecular weight (Mn). A polymer composed of molecules that are uniform with respect to their molecular weights is known as a monodisperse polymer and has a polydispersity value of one. A dendrimer is a monodisperse polymer because it has a well defined structure. On the other hand, high molecular weight hyperbranched polymers such as PEI have a broad molecular weight distribution with polydispersity in some cases greater than three. Since branched PG polymers are synthesized by ring-opening polymerization of NCA, they will inevitably possess a certain polydispersity. Similar to linear PG, the polydispersity (Mw/Mn) of branched poly(amino acids) is relatively narrow (PD=1.1–1.7), the values appeared to decrease with the increasing degree of polymerization. To achieve predictable biodistribution behaviors, narrow MWD is preferable for water-soluble polymeric carriers to be injected systemically. It is interesting to note that the hydrodynamic volumes of PEI-PG and PAMAM-PG$_n$ having number-average molecular weight (Mn) of 32,000 or higher are greater than the renal clearance threshold (4.5 nm). Thus the polymers are suitable for intravenous administration (Table 3).

Figure 3:
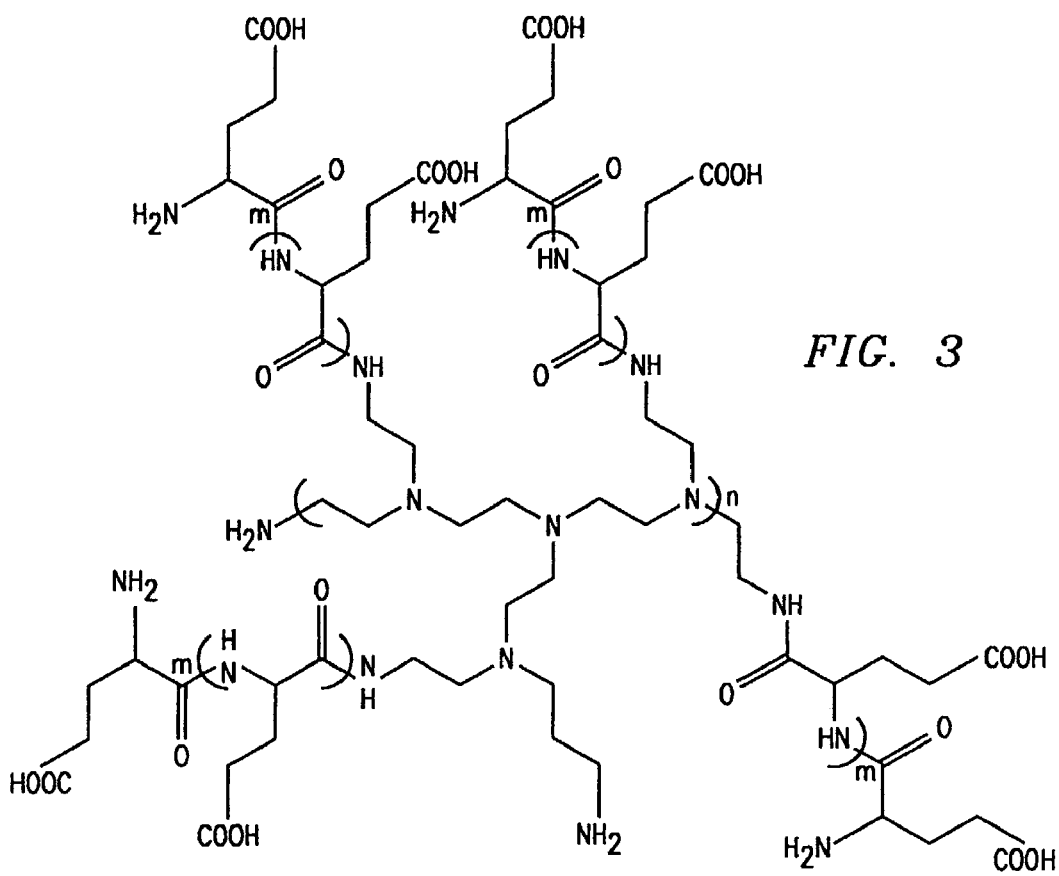
FIG. 3 illustrates one structure of branched PEI-poly(L-glutamic acid) according to an embodiment of the present invention.
Figure 4:
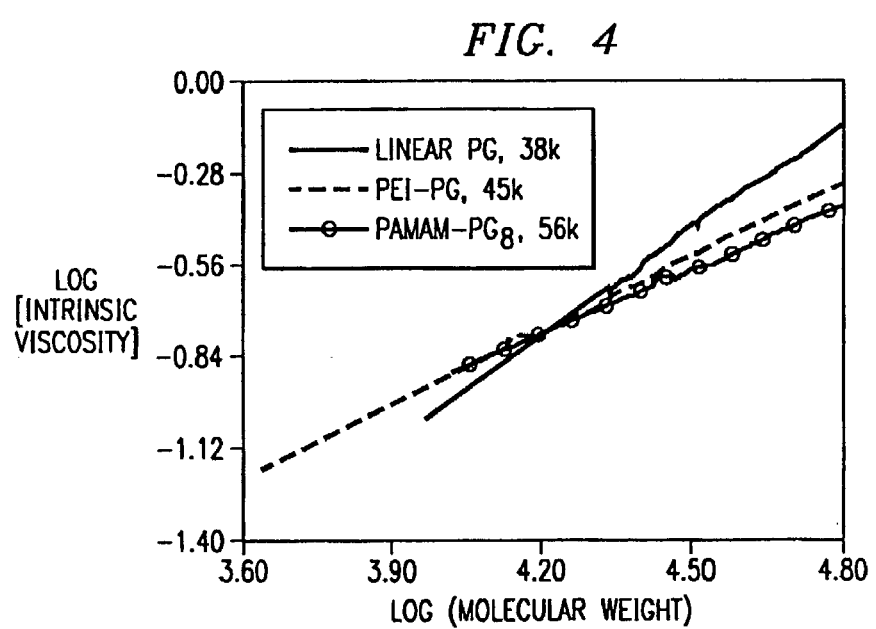
FIG. 4 illustrates Mark-Houwink plots of linear PG (Mw 36K), PEI-PG (Mw 45K), and PAMAM-PG8 (Mw 56K), as used in embodiments of the present invention.
Figure 8:
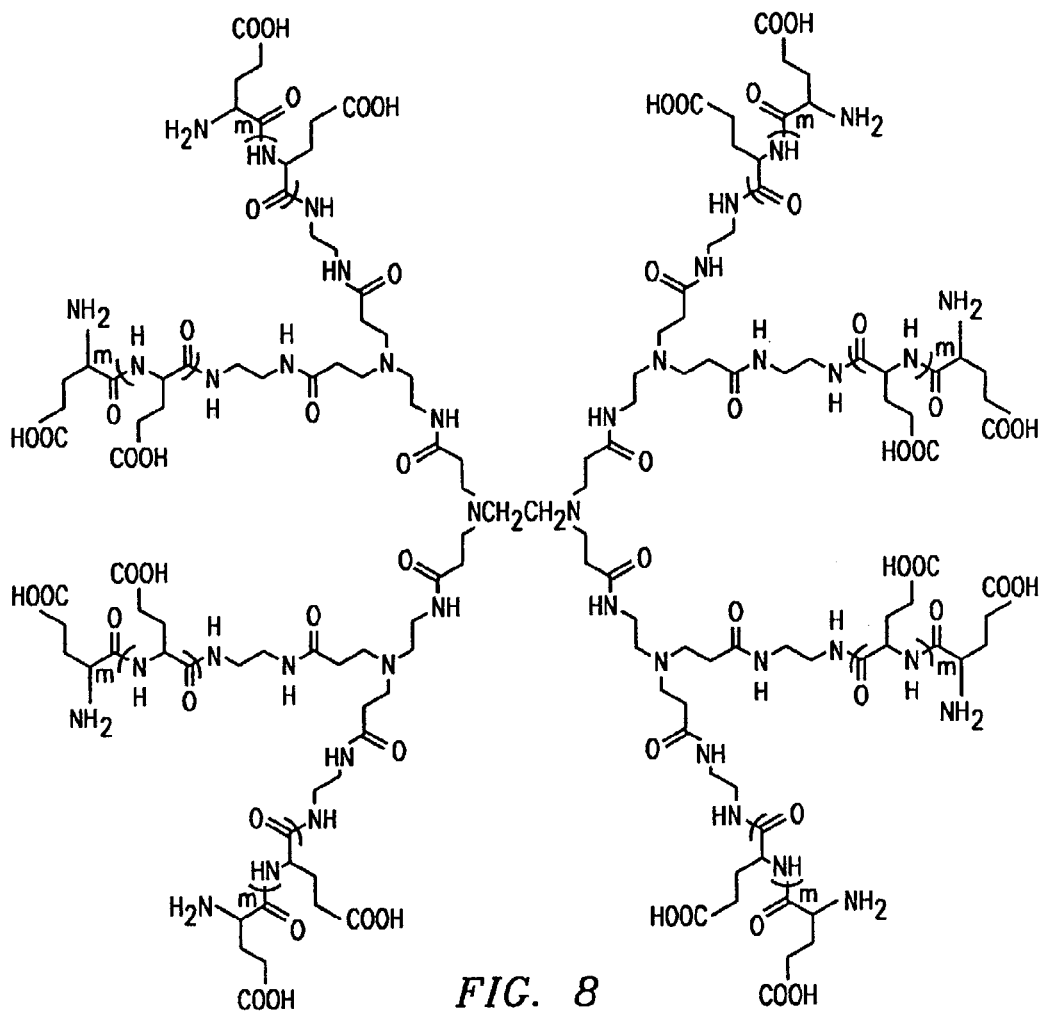
FIG. 8 illustrates the structure of nonlinear PAMAM-PG8, according to an embodiment of the present invention wherein different functional groups are present at the termini of polymer chains (—NH2) and the side chains of branching poly(L-glutamic acid) (—COOH)

The Mark-Houwink plot, which depicts the inverse of molecular density (or intrinsic viscosity) as a function of molecular weight, is used to describe structural differences among different polymers. Mark-Houwink plots of PAMAM-PG$_8$, PEI-PG, and linear PG in PBS are given in FIG. 4. The slope (commonly referred as the "a" value) is related to the way chains are added to the backbone of the molecule. Spherical structures will have a slope of zero, where as rod-like molecules will have a slope of two. For random coiled molecules the values a=0.5–0.8 is expected. Linear PG polymers have rather high "a" value, indicating that the molecules are rigid random coils, probably as a result of the electrostatic interaction. Although both PAMAM-PG$_8$ and PEI-PG are highly charged and the electrostatic repulsion should be operative as in linear polymers, their "a" values regardless of molecular weights are all smaller than that of linear PG (FIG. 4, Table 3). These data suggest that both PEI-PG and PAMAM-PG$_8$ resume long chain branched structures. Furthermore, when the numbers of branching PG chains increased from eight in PAMAM-PG$_8$ to sixteen in PAMAM-PG$_{16}$, the "a" value decreased from approx. 0.66 to 0.27, suggesting that the nonlinear polymers adopted a more globular-like structure when the number of PG arms was increased. The intercept value (referred as the "k" value) in the Mark-Houwink plot directly relates to the density of the backbone structure per repeating unit length. The branched polymers especially those with higher molecular weights have greater "k" values than that of linear PG polymers, indicating that these polymers are more densely packed than their linear counterparts (Table 3). It is interesting to note that the compactness of the nonlinear polymers increased drastically when the number of PG arms increased from eight to sixteen (Table 3). Thus both PEI-PG and PAMAM-PG$_n$ resume the "octopus" structure as depicted in FIG. 3 and FIG. 8.

Example 2

Conjugation of the Drug Paclitaxel to PAMAM-PG

Paclitaxel was conjugated to PAMAM-PG according to Li et al. (1998). Briefly, to a solution of PAMAM-PG$_8$ (150 mg, 1.16 mmol, Mn=48,800) in 5 ml dry DMF and 1 ml pyridine was added paclitaxel (93 mg, 0.11 mmol), diisopropylcarbodiimide (27.5 mg, 0.218 mmol), and a trace amount of dimethylaminopyridine. The reaction was allowed to proceed at room temperature overnight. Thin-layer chromatography (silica plate, eluent CHCl$_3$:MeOH=10:1) showed complete conversion of paclitaxel (R$_f$=0.55) to polymer conjugate (R$_f$=0). The solvents were evaporated under vacuum to one half of the volume, treated with 3.0 ml of 1 M NaHCO$_3$, and dialyzed overnight against water. After filtration through a 0.45 p filter, the solution was lyophilized to yield 250 mg of a light fluffy solid. Paclitaxel content: 28.6% (w/w, UV method). Yield (conversion to polymer bound paclitaxel, UV): 77%.

Example 3

Conjugation of the Diagnostic Agent Ioxilan to PEI-PG

Figure 5:
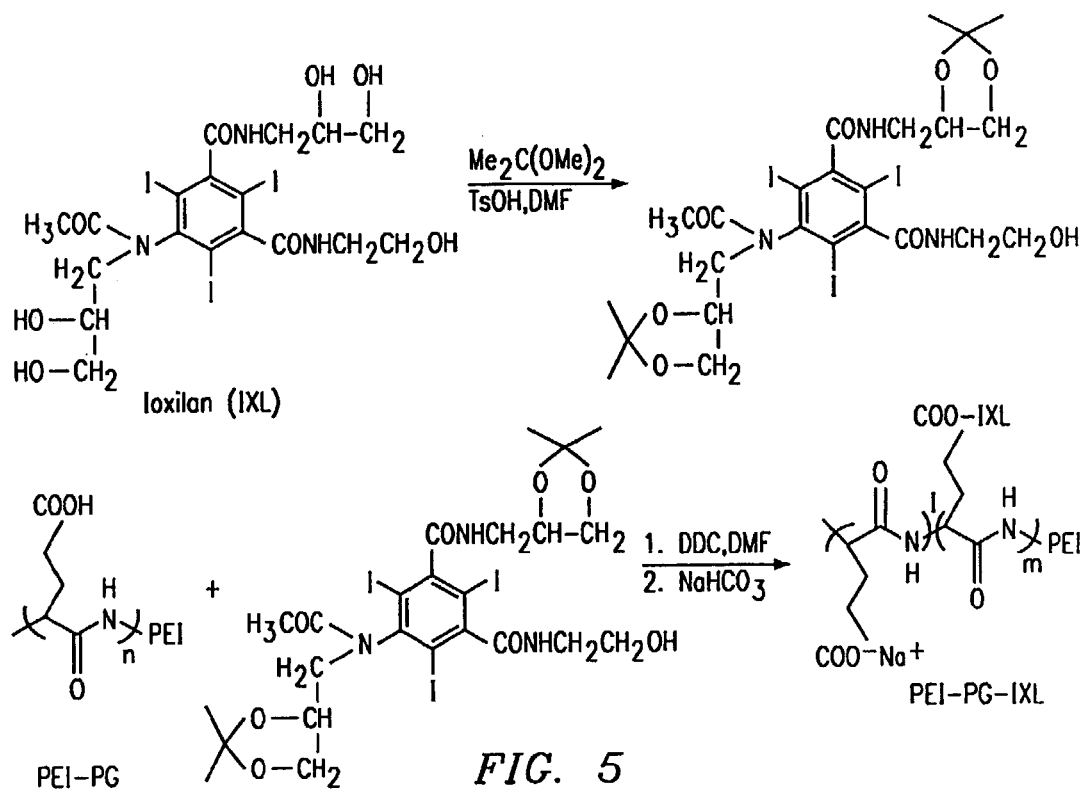
FIG. 5 illustrates a method of synthesis of 1,2-acetonide protected Ioxilan (IXL) and its conjugate with PEI-PG, according to an embodiment of the present invention.

CT is a major imaging modality with unsurpassed spatial and temporal resolution, and is widely used in diagnostic procedures. In current clinical practice, low-molecular-weight radiopaque iodine-containing organic compounds are used as CT contrast agents. However, there is a great need to develop clinically acceptable radiopaque macromolecular contrast agent as a blood-pool imaging agent. Ioxilan (IXL) is a triiodobenzoyl derivative that is used clinically as a small-molecular weight, non-ionic contrast agent. Ioxilan was conjugated to PEI-PG to demonstrate that a high payload of the contrast agent to the polymer may be achieved without compromising the aqueous solubility of the resulting conjugate. The two 1,2-diols in Ioxilan were first protected with acetonides by reacting with acetone dimethyl acetal in DMF in the presence of p-toluenesulfonic acid. PEI-PG-IXL was then synthesized using a dicyclohexylcarbodiimide-mediated coupling reaction between PEI-PG (Mw 150K) and acetonide-protected Ioxilan (FIG. 5). The product was purified by extensive dialysis, and by re-precipitation with 0.1 N HCl. PEI-PG-IXL thus obtained contained 17.6% (w/w) of iodine (54% Ioxilan, w/w) and was highly water-soluble. A solution of 100 mg of polymer conjugate/ml water (17.6 mg I/ml) could be easily prepared and handled. Such a solution should provide adequate CT contrast enhancement for the vasculature.

Example 4

Conjugation of Herceptin, a Targeting Ligand to PAMAM-PG

As discussed previously, many targeting ligands may be designed to have sulfhydryl groups (SH) introduced at specific sites, and this property may be used to operatively attach targeting ligands to the dendritic poly(amino acid) carriers if they contain SH-reactive groups. To illustrate that targeting moieties containing SH functional groups may be introduced to the chain ends of activated PG polymers, SH-reactive vinyl sulfonyl groups were conjugated to the termini of branched PG polymers with a PEG spacer, and the targeting ligand, Herceptin, was subsequently conjugated to the polymer through a selective sulfhydryl/vinylsulfone coupling reaction.

Into a solution of PAMAM-PG$_8$ (100 mg, Mw 53K) in phosphate buffered saline (0.1 M, pH=7.4) was added a total of 100 mg of VS-PEG-NHS in 5 fractions during a course of 5 hrs. The reaction mixture was allowed to stir overnight at room temperature. The extent of the reaction was followed by ninhydrin test, which showed a decrease in the concentration of free amine. The solution was treated with 1N HCl, and the precipitate was isolated by centrifugation at 3000 rpm for 5 min. The precipitate was washed twice with water and then lyophilized. GPC analysis showed an increase in the hydrodynamic radius from 6.32 nm to 6.76 nm, while the Mark-Houwink "a" value decreased from 0.542 to 0.323, and "k" value increased from 0.84 to 12.2. These data suggest further derivatization of PAMAM-PG by VS-PEG resulted in a more compact structure. The retention time in GPC chromatogram for VS-PEG-PAMAM-PG was 10.32 min, while the retention time for VS-PEG-NHS was 16.50 min. No free VS-PEG was detected in the purified product. Hydrogenl-based nuclear magnetic resonance ($^1$H-NMR) ($D_2O$) spectra showed characteristic chemical shifts for both PG and PEG molecules: 2.13 (m, 2H, β-$CH_2$ in PG); 2.47 (m, 2H, γ-$CH_2$ in PG); 4.24 (m, 1H, α-CH in PG); 3.71 (s, 1.5 H, $CH_2O$ in PEG). Based on the ratios of the integral values between PEG and PG, about two PEG chains were attached to each PAMAM-PG.

Figure 6:
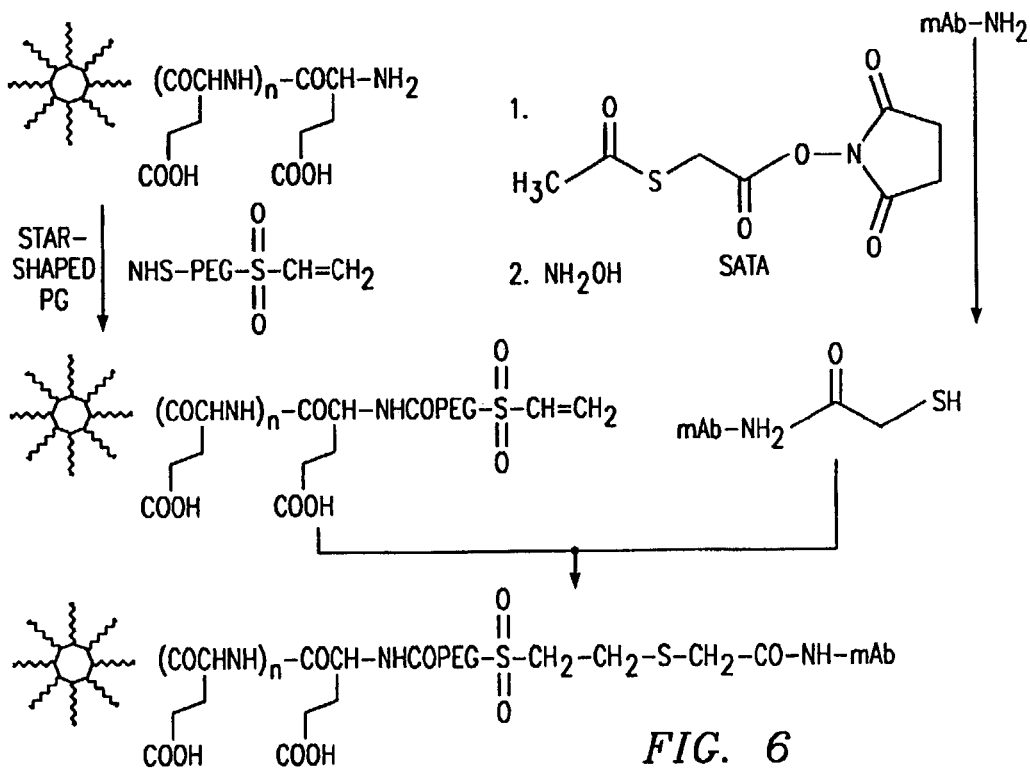
FIG. 6 illustrates a method of introduction of functional groups to the termini of branched PG and site-selective conjugation of monoclonal antibody (mAb) to the activated polymer for targeted drug delivery, according to an embodiment of the present invention.

Herceptin, a monoclonal antibody directed against Her-2/neu receptor, was conjugated to PAMAM-PG-block-PEG-VS through selective sulfhydryl/vinylsulfone coupling reaction (FIG. 6). Herceptin in PBS buffer (pH=7.2, 50 mg) was treated with N-succinimidyl S-acetylthioacetate (SATA, 8 mg/mL DMF, molar ratio 1:20) at room temperature for 1 hr, followed by aqueous hydroxylamine (50 M, 100 µL) for 2 hrs. The solution was concentrated by ultracentrifugation (molecular-weight-cut-off 10,000) to 1–2 mL, and purified with a PD-10 column. The decrease in free amino groups in the antibody during the course of treatment with SATA was monitored by TNBS assay, and the generation of SH group after treatment with hydroxylamine was monitored using Ellman's reagent. VS-PEG-PG was added to the solution of SH-Herceptin and the reaction mixture was allowed to stand at 4° C. overnight. The conjugate was first purified with affinity column to remove unconjugated polymer (Freezyme conjugate purification kit, Pierce Biotechnology, Inc., Rockford, Ill.), followed by anion-exchange chromatography (Amersham Pharmacia Biotech., Piscataway, N.J.) on a Fast Protein Liquid Chromatography (FPLC) system. The fractions collected from FPLC had retention time different from that of native Herceptin but still contained protein as determined by a protein assay, indicating that Herceptin was chemically conjugated to PEG-PG polymer conjugate. A similar approach may be adapted for the conjugation of Herceptin or other proteins to PEI-PG or PAMAM-PG functionalized at their termini with vinylsulfone or other functional groups.

Example 5

Conjugation of the Polymer PEG to PAMAM-$PG_8$

PEG may be conjugated to the branched PG polymers either by grafting to the side chains of PG or by attaching to the termini of PG. To synthesize PEG-grafted copolymer, 400 mg of PAMAM-$PG_8$ ($M_n$=69.5 K, 3.10 mmol glutamic acid repeating unit) was dissolved along with 400 mg of methoxyl PEG ($M_n$=5 K, 0.0.8 mmol), 63.1 mg diisopropylcarbidiimide (0.50 mmol) and 2.0 mg of 4-dimethylaminopyridine in 40 ml of dimethylformamide and 4.0 ml of pyridine. The solution was stirred at room temperature overnight. The solvent was evaporated under vacuum and the residual was redissolved in 10 ml of 1.0 M $NaHCO_3$, dialyzed against water (10K molecular weight cut off). Attempt to pass the solution through 0.45 µm filters was only achieved with great difficulty, suggesting that crosslink of the polymers occurred during the reaction. $^1$H-NMR spectrum reviewed peaks associated with both PG and PEG blocks. Analysis based on integrals of $C_\alpha H$ of PG and $CH_2CH_2O$ of PEG indicated that each copolymer contained approximately 18 PEG chains. The number-average molecular weight (Mn) of PAMAM-$PG_8$-graft-PEG was 668 K as determined by GPC-triple detector system. This value was much higher than the calculated value of 160 K based on 18 PEG chains, again suggesting crosslink of polymers.

To synthesize dendritic poly(amino acid) with PEG terminated at the chain ends, an aqueous solution of methoxyl PEG nitrophenylcarbamate (Mn=5050, 200 mg, 0.0396 mmol) was added into an aqueous solution of branched PEI-PG sodium salt (Mn=9500, 100 ml, 0.0105 mmol repeating units, pH 7–8). The mixture was stirred at room temperature for 48 h. The solution was dialyzed against water overnight, filtered through a 0.45 m filter and lyophilized to yield 255 mg of white material. The yellow nitrophenol was removed from the product during dialysis. $^1$H-NMR spectrum reviewed peaks associated with both PG and PEG blocks. The number-average molecular weight of PEI-PG-block-PEG was 11,100 K as determined by GPC-triple detector system. Data indicates that grafting to the side chains often results in crosslink of copolymers, as in the case of PAMAM-$PG_8$-graft-PEG, whereas coupling through the terminal amine functional groups completely avoids polymer crosslink.

Example 6

Cytotoxicity Study Using PAMAM-$PG_8$ Conjugated to Paclitaxel (PAMAM-$PG_8$-TXL)

Figure 9:
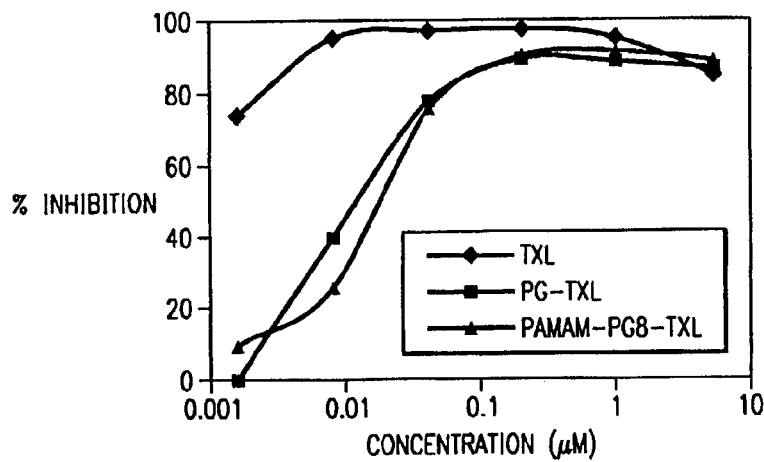
FIG. 9 illustrates the growth inhibition of A431 cells by water-soluble polymer-paclitaxel (TXL) conjugates after a 72-h continuous exposure as determined by MTT assay, according to an embodiment of the present invention wherein the concentrations indicated are equivalent TXL concentrations.

The MTT assay was used to quantitatively compare the effects of PAMAM-$PG_8$-TXL, linear PG-TXL, and paclitaxel on cell growth in a human vulvar squamous A431 cell line. Cells were plated in a 96-well plate at a density of 2000 cells/well and then incubated with various concentrations of paclitaxel, PAMAM-$PG_8$-TXL, or linear PG-TXL. After 72 hrs of continuous drug incubation, 50 µl of 3 mg/ml MTT [(3,4-dimethylthiazol-2-yl-2,5-diphenyltetrazolium bromide] (Promega, Madison Wis.) was added to each well, and the plate was incubated for an additional 4 h. The culture medium was removed by aspiration, and 200 µl of DMSO was added to each well to dissolve the cells. The optical absorbance was measured at 540 nm, using a micro-plate reader (Molecular Devices Corporation, Sunnyvale, Calif.). The data were reported as the means of quadruplicate measurements. The standard errors of the mean were less than 15%. As demonstrated in FIG. 9, paclitaxel, PAMAM-$PG_8$-TXL and linear PG-TXL showed a similar concentration-dependent growth inhibition within each cell line. The cells were more sensitive to the parent drug paclitaxel with an estimated $IC_{50}$ value of less than 1.0 nM. This is consistent with the notion that the toxic effect of chemotherapeutic agents was reduced upon conjugation with polymers. This feature is important for reduced systemic toxicity after administration of polymeric drug. The cells exhibited similar sensitivity to PAMAM-$PG_8$-TXL and linear PG-TXL with estimated $IC_{50}$ values of 20 nM for both agents, suggesting that both conjugates behave as prodrugs of paclitaxel (Oldham et al., 1999). However, as discussed previously, branched and nonlinear PG possess additional features that allow conjugation of multiple targeting moieties at the end of polymer chains without causing crosslink of polymers, and thus this type of poly(amino acids) are suitable for targeted drug delivery. PAMAM-PG$_8$ polymer alone is not cytotoxic at polymer concentration of up to 10 mg/ml (data not shown).

Example 7

In Vivo CT Study Using the PEI-PG with Conjugated Ioxilan

Figure 7:
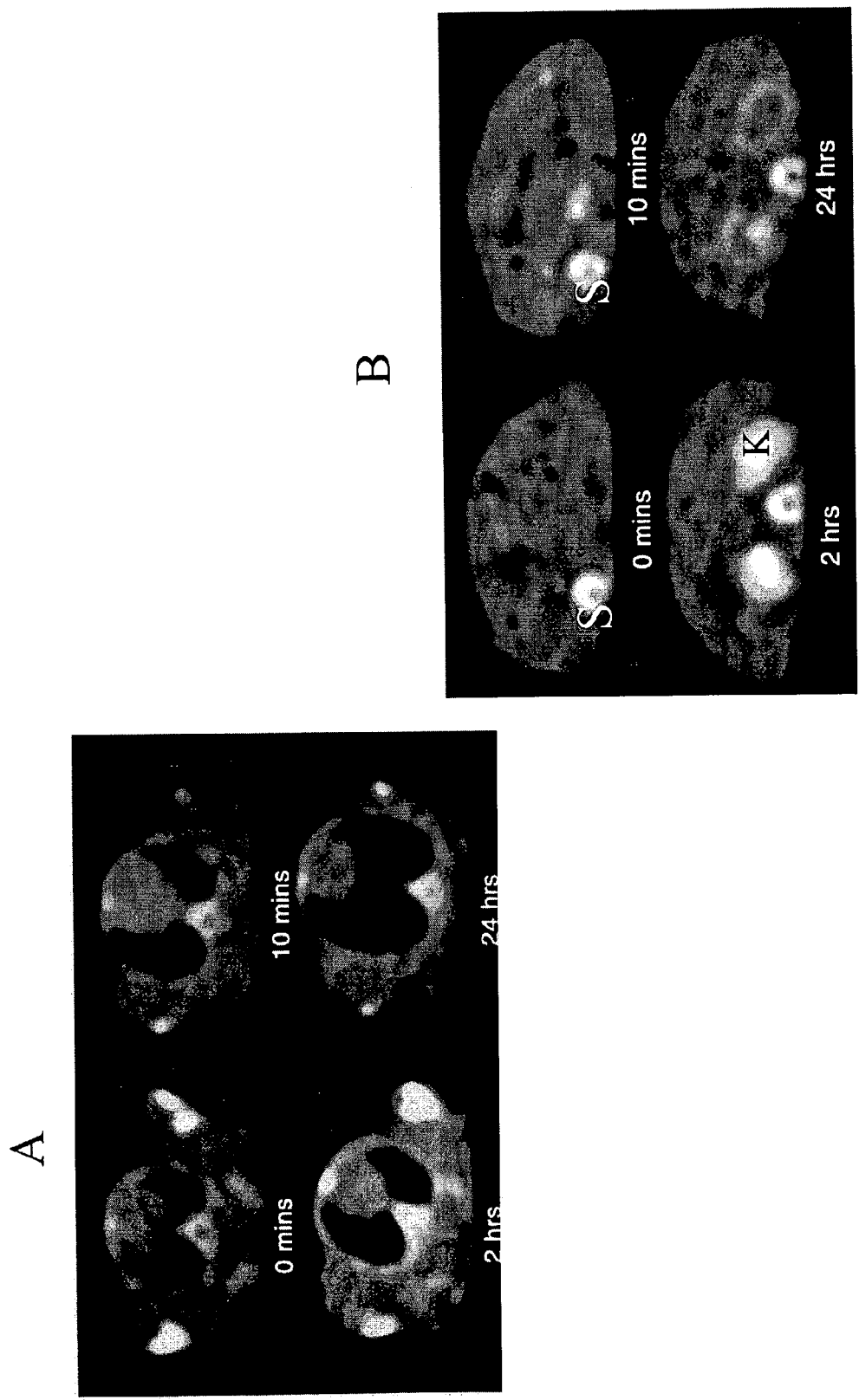
FIGS. 7A and 7B illustrates a CT section series of a mouse after intravenous administration of PEI-PG-IXL at 238 mg I/kg, according to an embodiment of the present invention, wherein transverse sections were chosen in the regions of heart FIG. 7A and kidney FIG. 7B (K: kidney, S: spine)

To obtain information on biodistribution, the polymer solution (100 mg/ml) filtered through a 0.45 μm filter, was injected intravenously into nude mice (22 g, pentobarbital anesthesia, 50 mg/kg, i.p) at a dose of 235 mgI/kg. Chest and abdominal CT images were acquired at 10, 60, 120 min and 24 h post-injection using GE HighSpeed Advantage scanner (GE, Milwaukee, Wis.). On the images from each time point, signal intensities of heart (blood), liver, and kidney were determined using region-of-interest. Significant enhancement of blood pool (heart) and kidney was observed for a prolonged period of time after injection (See FIG. 7, Table 4 below). Increased opacity of the heart may be visualized for up to 2 hrs (FIG. 7). The contrast agent was largely excreted through the kidney (FIG. 7). Interestingly, liver opacity only increased moderately during the first hour after injection.

TABLE 4

Organ Opacification in Mice after Injection of Iodinated Polymer PEI-PG-IXL*

| Time | Heart | Liver | Kidney | Muscle | Tumor |
|---|---|---|---|---|---|
| 0 min | 71 ± 3 | 88 ± 9 | 79 ± 6 | 93 ± 4 | 56 ± 4 |
| 10 min | 155 ± 11 | 112 ± 9 | 139 ± 5 | 86 ± 8 | 66 ± 10 |
| 60 min | 104 ± 6 | 100 ± 5 | 238 ± 32 | 82 ± 8 | 66 ± 15 |
| 120 min | 94 ± 15 | 89 ± 12 | 182 ± 15 | 73 ± 7 | 65 ± 9 |
| 24 h | 82 ± 9 | 92 ± 16 | 166 ± 63 | 79 ± 5 | 75 ± 9 |

*Data are expressed in Hounsfield units (HU, mean ± SD) within region of interest in 3 mice.

Example 8

Figure 10:
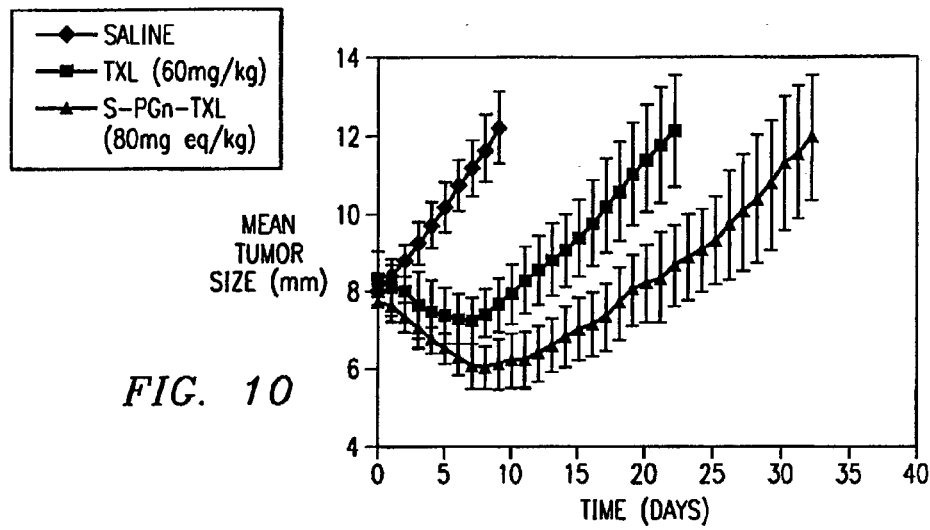
FIG. 10 illustrates antitumor activity of S-PGn-paclitaxel conjugate compared to paclitaxel and Cremophor vehicle in C3Hf/kam mice bearing syngeneic murine ovarian OCA-1 tumor, according to an embodiment of the present invention.
Figure 11:
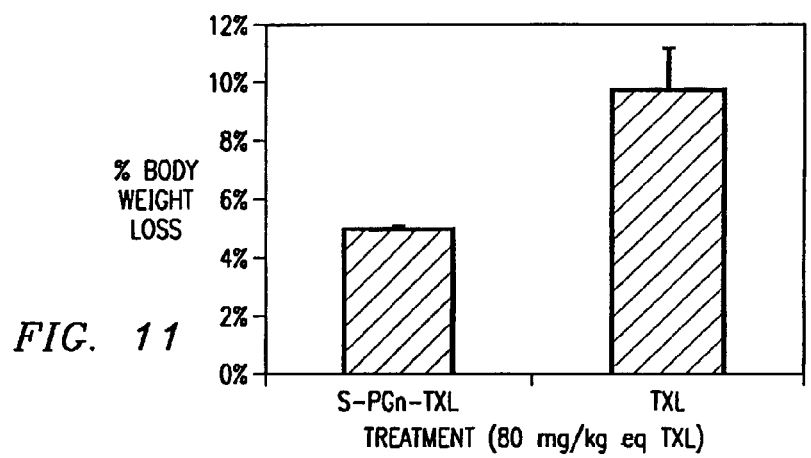
FIG. 11 illustrates a comparison of body weight loss after treatment with S-PGn-paclitaxel or paclitaxel at their respective dose levels of 80 mg/kg eq and 60 mg/kg eq TXL, according to an embodiment of the present invention.
Figure 12:
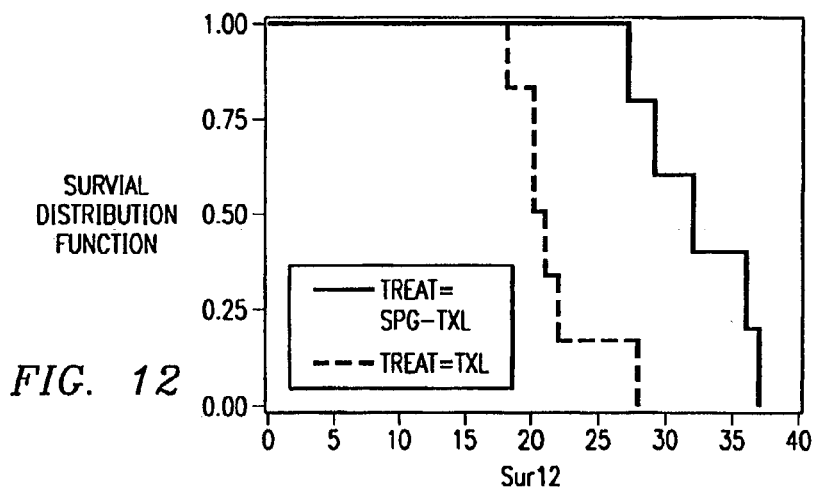
FIG. 12 illustrates the survival distribution function for tumor size from 8–12 mm in C3Hf/kam mice bearing syngeneic murine ovarian OCA-1 tumor, after treatment with paclitaxel alone or S-PGn-paclitaxel, according to an embodiment of the present invention.

Effects of Delivering Paclitaxel Using Dendritic Poly(Amino Acids) to C3Hf/kam Mice Bearing Syngeneic Murine Ovarian OCA-1 Tumor To evaluate the ability of star shaped PG (S-PG$_n$, wherein n designates the number of polyglutamic acid arm) to carry water-insoluble drugs, paclitaxel was conjugated to S-PG$_8$ using carbodiimide-mediated reaction. The resulting conjugates contained 20–25% paclitaxel (w/w) and were highly water-soluble (>20 mg eq. paclitaxel/ml). The antitumor effects of S-PG$_n$-paclitaxel and paclitaxel were determined by their ability to delay tumor growth in C3Hf/kam mice bearing syngeneic murine ovarian OCA-1 tumor. When the tumors had reached 8 mm in average diameter, S-PG$_8$-paclitaxel or paclitaxel was injected intravenously in a single dose. S-PG$_n$-paclitaxel at an equivalent paclitaxel dose of 80 mg/kg caused an absolute growth delay of 24 days, whereas paclitaxel at a dose of 60 mg/kg caused a growth delay of only 14 days. See FIGS. 10 and 12. At their respective dose levels, S-PG$_n$-paclitaxel caused a maximum of 4.5% body weight loss whereas paclitaxel caused 10% body weight loss. See FIG. 11. Data indicates that S-PGn-paclitaxel is very efficacious against OCA-1 tumor with reduced toxicity, and that S-PGN may be a promising new class of polymers suitable for targeted drug delivery.

Example 9

Conjugation of Targeting Ligand Folic Acid to Termini of PAMAM-PG$_{16}$ Indocyanine Dye as a Diagnostic Agent to the Side Chains of PAMAM-PG$_{16}$ for Near Infrared Optical Imaging 18.6 mg (0.15 mmol) of diisopropylcarbodiimide was added to a solution of 75 mg (0.003 mmol) of PAMAM-PG$_{16}$ (MW 25,000) an 48 mg (0.1 mmol) of folic acid (FA) in dimethylsulfoxide (DMSO). The reaction was stirred overnight and then treated with 5.0 ml of 1M NaHCO$_3$. This mixture was dialyzed against water overnight at 4° C. (molecular weight cut-off, 10K). The resulting solution was filtered through a 0.45 μm filter and lyophilized to yield 101.4 mg of yellow material. The lyophilized material was further purified with a PD-10 column. Fractions containing PAMAM-PG$_{16}$ polymer were combined and dialyzed against water overnight, filtered through a 0.45 μm filter and lyophilized to yield 65 mg of a cotton-like yellow material. A ninhydrin test for amines was negative, suggesting complete conversion of the terminal amino groups. The fractions from the PD-column were further analyzed by GPC. No free folic acid was detected in the purified product. The conjugate contained 5% folic acid by weight, approximately 3 folic acid molecules were attached to each PAMAM-PG$_{16}$ polymer.

Figure 13:
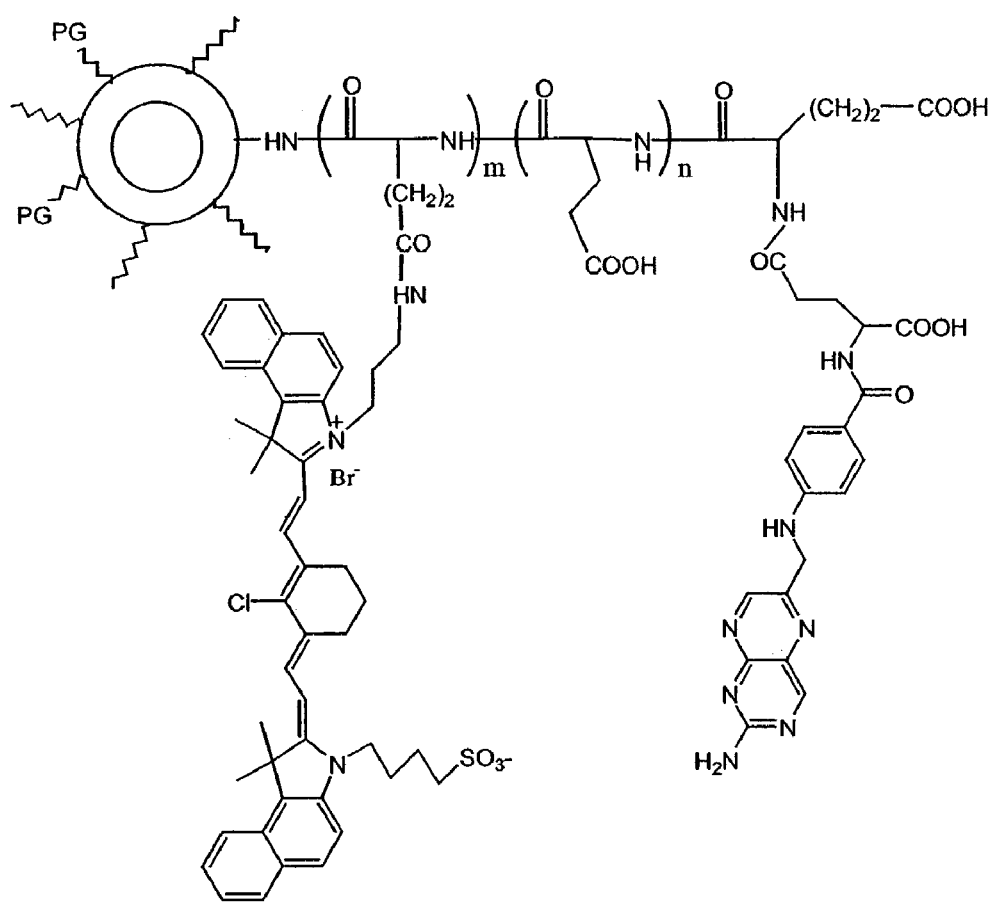
FIG. 13 illustrates the structure of nonlinear PAMAM-PG8 according to an embodiment of the present invention wherein folic acid functional groups are present at the termini of the polymer chains (—$NH_2$) and dye molecules ICG-$NH_2$ are present as side chains.

The sodium salt form of PAMAM-PG$_{16}$—FA conjugate (60 mg) obtained as above was converted to its acid form by acidification with HCl solution. The resulting yellow-orange solid was dissolved in 2.0 ml DMSO. To this solution was added 4.6 mg (0.04 mmol) of N-hydroxysuccinimide, followed by 6.0 mg (0.047 mmol) of diisopropylcarbodiimide, and the reaction was allowed to proceed for 30 min. A DMF solution of an indocyanine fluorescent dye derivative ICG-NH$_2$ (3.0 mg, 0.003 mmol) was subsequently added into the reaction mixture and the reaction was allowed to proceed overnight. To stop the reaction, 2.0 ml of 1.0 M NaHCO$_3$ was added into the reaction mixture. The mixture was dialyzed against water, filtered through a 0.45μ filter, and then lyophilized to yield 33 mg of a dark green solid. The conjugate contained 9% (w/w) of the ICG-NH$_2$ dye, or approximately 3 dye molecules per macromolecule. FIG. 13 shows the structure of PAMAM-PG$_{16}$-ICG-folate conjugate containing folic acids at the termini of the polymer and dye molecules ICG-NH$_2$ at the side chains of the polymer.

The folic acid receptors (FR)-mediated binding of near-infrared gluorescent conjugate PAMAM-PG$_{16}$-ICG-folate was studied using a human nasopharyngeal epidermal carcinoma cell line KB and a human breast carcinoma cell line SK-BR3. KB cells over-express the FR, whereas SK-Br3 cells have no detectable FA. Cells were incubated with PAMAM-PG$_{16}$-ICG-folate, indocyanine green (ICG, Sigma-Aldrich Corp. St. Louis, Mo.) or ICG-NH$_2$ at 37° C. on cover clips in a 24-well place (Beckton Dickinson Labware, Franklin Kakes, N.J.). Each well contained 0.5 ml Dulbecco's Modified Eagle's medium/nutrient Mixture F-12 Ham (DMEM/F12) containing 10% FBS (Gibco, Grand Island, N.Y.). The final concentration of the conjugate was calculated based on the equivalent does of folic acid and ICG-NH$_2$. For the blocking study, free folic acid was added to the culture medium 30 minutes prior to the addition of the test agents. Cells were washed twice with PBS at the end of incubation (30 minutes) and fixed in 95% ethyl alcohol. The cells were treated with 1 μM Sytox Green (Molecular Probe, Eugene, Oreg.) for 15 minutes to stain the cell nuclei and washed twice with PBS. Data were recorded by a Leica DMR microscope (Leica Microsystems Inc. Brannockburn, Ill.) equipped with a 75 W Xenon lamp, Indo-Cyanine Green and FITC filters (775/845 and 480/535, excitation/emission, respectively) (Chroma Technology Corp., Brattleboro, Vt.), Hamamatsue B/W Chilled CCD camera (Hamamatsu Photonics, K.K. Hamamamatsu City, Japan) and Image-Pro Plus 4.5.1 software (Media Cybernetics, L. P., Silver Spring, Md.). ICG was assigned to green color and Sytox Green was assigned to red color.

Figure 14A:
FIG. 14 illustrates fluorescent microscopic images at original magnification of ×20 objective of SK-Br3 cells after 30 minute incubation with various near-infrared dyes, according to an embodiment of the present invention, wherein red indicates Syntox Green stain for cell nuclei and green indicates indocyanide derivatives.
Figure 14B:
Figure 14C:
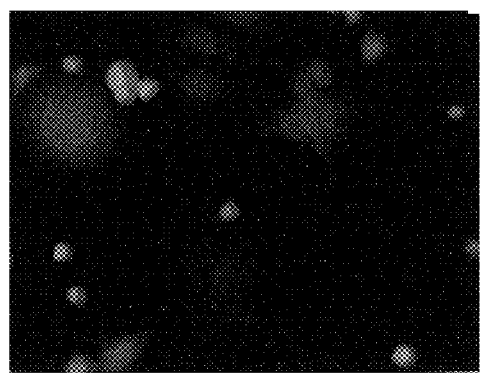
Figure 15A:
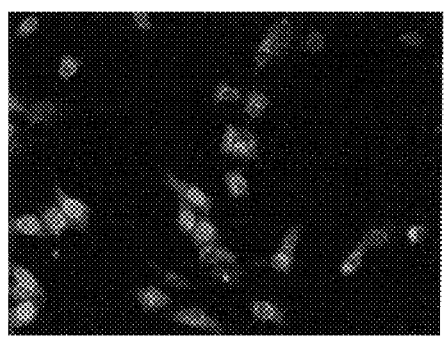
FIG. 15 illustrates fluorescent microscopic images at original magnification of ×20 objective of KB cells after 30-minute incubation with various near-infrared dyes, according to an embodiment of the present invention, wherein red indicates Syntox Green stain for cell nuclei and green indicates indocyanide derivatives.
Figure 15B:
Figure 15C:
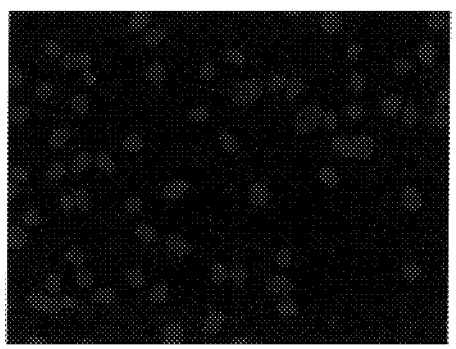
Figure 15D:

FIG. 14 shows the fluorescent images of SK-Br3 cells that do not express folate receptors on the cell surfaces. The commercially available indocyanine green dye (ICG) did not have detectable non-specific interaction with these cells. ICG derivatives containing an amino group ICG-$NH_2$ has strong non-specific interaction with the cell membrane, probably as a result of its increased lipophilic characteristics. However, when ICG-$NH_2$ was conjugated to PAMAM-$PG_{16}$, no fluorescence was detected, suggesting that the nonlinear PG polymers were able to suppress the non-specific interaction of dye molecules with cell membranes. When folic acid was conjugated to the termini of PAMAM-$PG_{16}$ to produce PAMAM-$PG_{16}$—ICG-FA, there was no detectable fluorescence in SK-Br3 cells (which do not express FR), as shown in FIG. 14.

However, the green fluorescence from targeted polymer-bound dye was visualized in KB cells that express FR when the cells were incubated with PAMAM-$PG_{16}$-ICG-FA for 30 minutes. See FIG. 15. Qualitatively, the binding was very strong because even a large excess of FA could not completely block the interaction between PAMAM-$PG_{16}$-ICG-FA and the KB cells. A conjugate of FA and ICG-$NH_2$, labeled FA-ICG, did not bind to KB cells, suggesting that conjugation of ICG-$NH_2$ directly to FA destroyed FA's capacity to bind FR. See FIG. 15.

Thus, nonlinear PG polymers may reduce undesirable non-sepcific interaction of diagnostic and therapeutic agents with non-target cells. Additionally, the binding affiinity of targeting molecules in the present invention is preserved and even enhanced by their attachment to the termini of nonlinear polymers.

Example 10

Degradation of PAMAM-PG by Lysosomal Enzyme Cathepsin B

PAMAM-$PG_8$ or PAMAM-$PG_{16}$ was dissolved in PBS buffer (pH 5) at a concentration of 8 mg/ml at room temperature. Cathepsin B was added to the above solution at a concentration of 10 units/ml. Aliquots of the polymers were taken at various time intervals and were injected into a Water HPLC system including a G3000PW gel permeation chromatography column (Tosohaas) and a Viscotek E-$Z^{Pro}$ triple detector array (Houston, Tex.). The mobile phase (0.1 mM PBS buffer, pH 7.4 containing 0.1% LiBr, w/v) was run at a flow rate of 1 ml/minute.

Figure 16:
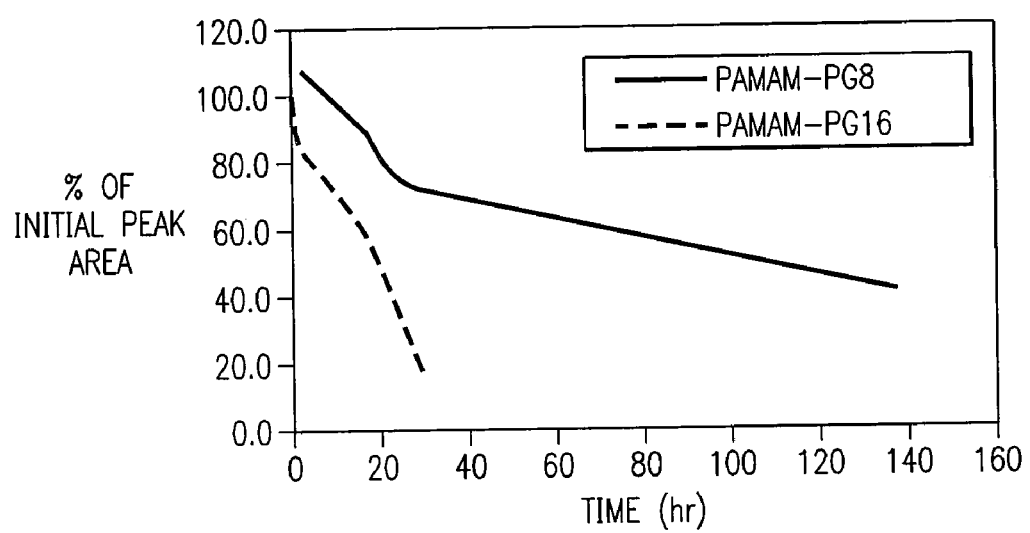
FIG. 16 illustrates biodegradation of nonlinear PG polymers, according to an embodiment of the present invention, by cathepsin B enzyme.

The peak areas attributable to both PAMAM-$PG_8$ or PAMAM-$PG_{16}$ in the GPC chromatograms decreased with increasing incubation time (data not shown). However, the degradation of PAMAM-$PG_{16}$ was much faster than that of PAMAM-$PG_8$. FIG. 16 depicts the function of time after incubation with Cathepsin solution. PAMAM-$PG_{16}$ had about 20% undegraded polymer after 20 hours, whereas PAMAM-$PG_8$ had about 40% undegraded polymer by 137 hours. This indicates that the nonlinear PG of the present invention is biodegradable, and that the number of arms of the nonlinear PG polymers affects the rate of polymer degradation.

All of the compositions and methods disclosed and claimed herein may be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of synthesizing a dendritic poly(amino acid) comprising:
    combining blocked NCA monomers of an amino acid and a PEI dendritic initiator in a solvent to form a reaction mixture; and
    incubating the reaction mixture for about 30 minutes to about 48 hours, wherein a blocked dendritic poly (amino acid) is obtained.

2. The method of claim 1, wherein the NCA monomer comprises glutamic acid.

3. The method of claim 1, further comprising conducting the incubation at a temperature range between 40° C. to 100° C.

4. The method of claim 1, further comprising deblocking side-chain protecting groups of the blocked dendritic poly (amino acid) to produce deblocked dendritic poly(amino acid).

5. The method of claim 4, wherein deblocking comprises bubbling HBr through the reaction mixture.

6. The method of claim 5, further comprising bubbling HBr though the reaction mixture for at least 30 minutes.

7. The method of claim 4, further comprising extracting the deblocked dendritic poly(amino acid) in a solvent.

8. The method of claim 1, wherein the dendritic poly (amino acid) comprises side chains of water-soluble functional groups.

9. The method of claim 8, wherein the water-soluble functional groups comprise an amino group.

10. The method of claim 1, wherein the PEI has a molecular weight of between 500 and 10,000.

11. The method of claim 1, wherein the PEI comprises between 2 and 250 amines suitable for initiating a polymerization reaction.

12. The method of claim 2, wherein the glutamic acid consists essentially of L-glutamic acid.

13. The method of claim 2, wherein the glutamic acid consists essentially of D-glutamic acid.

14. A method of synthesizing a dendritic poly(amino acid) comprising:
    combining blocked NCA momoners of an amino acid and a PEI dendritic initiator in a solvent to form a reaction mixture;
    incubating the reaction mixture for about 30 minutes to about 48 hours to from a blocked dendritic poly(amino acid); and
    deblocking side-chain protecting groups of the blocked dendritic poly(amino acid), wherein a deblocked dendritic poly(amino acid) is obtained, and wherein the deblocked dendritic poly(amino acid) comprises side chains of water-soluble functional groups.

15. The method of claim 14, wherein the NCA monomer comprises glutamic acid.

16. The method of claim 15, wherein the glutamic acid consists essentially of L-glutamic acid.

17. The method of claim 15, wherein the glutamic acid consists essentially of D-glutamic acid.

18. The method of claim 14, wherein the PEI has a molecular weight of between 500 and 10,000.

19. The method of claim 14, wherein the PEI comprises between 2 and 250 amines suitable for initiating a polymerization reaction.

20. The method of claim 14, further comprising conducting the incubation at a temperature range between 4° C. to 100° C.

21. The method of claim 14, wherein deblocking comprises bubbling HBr through the reaction mixture.

22. The method of claim 14, further comprising bubbling HBr though the reaction mixture for at least 30 minutes.

23. The method of claim 14, further comprising extracting the deblocked dendritic poly(amino acid) in a solvent.

24. The method of claim 14, wherein the dendritic poly(amino acid) comprises side chains of water-soluble functional groups, wherein the water-soluble functional groups comprise an amino group.

25. A method of synthesizing a dendritic poly(glutamic acid) comprising:

combining blocked glutamic acid momoners and a PEI dendritic initiator in a solvent to form a reaction mixture;

incubating the reaction mixture for about 30 minutes to about 48 hours to from a blocked dendritic poly (glutamic acid);

deblocking side-chain protecting groups of the blocked dendritic poly(glutamic acid); and extracting the deblocked dendritic poly(glutamic acid) in a solvent, wherein a deblocked dendritic poly(glutamic acid) is obtained, wherein the deblocked dendritic poly(glutamic) comprises side chains of water-soluble functional groups having amino groups.

26. The method of claim 25, wherein the glutamic acid consists essentially of L-glutamic acid.

27. The method of claim 25, wherein the glutamic acid consists essentially of D-glutamic acid.

28. The method of claim 25, wherein the PEI has a molecular weight of between 500 and 10,000.

29. The method of claim 25, wherein the PEI comprises between 2 and 250 amines suitable for initiating a polymerization reaction.

30. The method of claim 25, further comprising conducting the incubation at a temperature range between 4° C. to 100° C.

31. The method of claim 25, wherein deblocking comprises bubbling HBr through the reaction mixture.

32. The method of claim 25, further comprising bubbling HBr though the reaction mixture for at least 30 minutes.

33. The method of claim 1, wherein the NCA monomer comprises aspartic acid.

34. The method of claim 1, wherein the NCA monomer comprises lysine.

35. The method of claim 1, wherein the NCA monomers comprises an a combination of at least two NCA monomers selected from the group consisting of glutamic acid, aspartic acid and lysine.

36. The method of claim 8, wherein the water-soluble functional groups comprise a hydroxyl group.

37. The method of claim 8, wherein the water-soluble functional groups comprise an amino group and a hydroxyl group.

38. The method of claim 14, wherein the NCA monomer comprises aspartic acid.

39. The method of claim 14, wherein the NCA monomer comprises lysine.

40. The method of claim 14, wherein the NCA monomers comprises an a combination of at least two NCA monomers selected from the group consisting of glutamic acid, aspartic acid and lysine.

41. The method of claim 14, wherein the dendritic poly(amino acid) comprises side chains of water-soluble functional groups, wherein the water-soluble functional groups comprise a hydroxyl group.

42. The method of claim 14, wherein the dendritic poly(amino acid) comprises side chains of water-soluble functional groups, wherein the water-soluble functional groups comprise an amino group and a hydroxyl group.

* * * * *